(12) United States Patent
Lee

(10) Patent No.: US 11,369,355 B2
(45) Date of Patent: Jun. 28, 2022

(54) MEDICAL DEVICE AND SYSTEM FOR OCCLUDING A TISSUE OPENING AND METHOD THEREOF

(71) Applicant: Coherex Medical, Inc., Salt Lake City, UT (US)

(72) Inventor: Sung K. Lee, West Jordan, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 97 days.

(21) Appl. No.: 16/442,893

(22) Filed: Jun. 17, 2019

(65) Prior Publication Data

US 2020/0390428 A1 Dec. 17, 2020

(51) Int. Cl.
*A61B 17/00* (2006.01)
*A61B 17/12* (2006.01)

(52) U.S. Cl.
CPC .... *A61B 17/0057* (2013.01); *A61B 17/12122* (2013.01); *A61B 17/12163* (2013.01); *A61B 2017/00615* (2013.01); *A61B 2017/00628* (2013.01); *A61B 2017/00632* (2013.01); *A61B 2017/1205* (2013.01)

(58) Field of Classification Search
CPC ........ A61B 17/12031; A61B 17/12122; A61B 17/12159; A61B 2017/00615; A61B 2017/00628; A61B 2017/00632
See application file for complete search history.

(56) References Cited

U.S. PATENT DOCUMENTS

| 3,095,877 A | 7/1963 | Rowan |
| 3,874,388 A | 4/1975 | King et al. |
| 5,171,259 A | 12/1992 | Inoue |

(Continued)

FOREIGN PATENT DOCUMENTS

| CA | 2627408 | 5/2008 |
| DE | 102006056283 | 6/2008 |

(Continued)

OTHER PUBLICATIONS

European Search Report dated Aug. 6, 2018 for EP App. No. 18157669.5 (15 pages).

(Continued)

*Primary Examiner* — Thomas McEvoy
(74) *Attorney, Agent, or Firm* — David L. Stott

(57) ABSTRACT

Devices, methods and systems are provided for occluding a left atrial appendage. In one embodiment, a medical device includes a cover portion and a foam anchor portion with a flexible member coupled therebetween. The cover portion is configured to be positioned over an ostium of the left atrial appendage. The foam anchor portion extends between a proximal end and a distal end to define a length and an axis defined along the length of the foam anchor portion. The foam anchor portion defines a curved external surface radially extending relative to the axis such that the curved external surface extends between the proximal and distal ends of the foam anchor portion. The foam anchor portion is configured to self-expand to provide an outward biasing force from the curved external surface such that a circumferential surface area of the curved external surface biases against tissue of the left atrial appendage.

19 Claims, 10 Drawing Sheets

(56) References Cited

U.S. PATENT DOCUMENTS

| | | |
|---|---|---|
| 5,192,301 A | 3/1993 | Kamiya et al. |
| 5,284,488 A | 2/1994 | Sideris |
| 5,334,217 A | 8/1994 | Das |
| 5,425,733 A | 6/1995 | Schmieding |
| 5,425,740 A | 6/1995 | Hutchinson, Jr. |
| 5,433,727 A | 7/1995 | Sideris |
| 5,792,165 A | 8/1998 | Klieman et al. |
| 5,797,886 A | 8/1998 | Roth et al. |
| 5,861,003 A | 1/1999 | Latson et al. |
| 5,904,703 A | 5/1999 | Gilson |
| 5,910,154 A | 6/1999 | Tsugita et al. |
| 5,935,112 A | 8/1999 | Stevens et al. |
| 5,992,158 A | 11/1999 | Goddard et al. |
| 6,096,027 A | 8/2000 | Layne |
| 6,152,144 A * | 11/2000 | Lesh .................. A61B 17/0057 128/898 |
| 6,174,322 B1 | 1/2001 | Schneidt |
| 6,231,561 B1 | 5/2001 | Frazier et al. |
| 6,238,403 B1 | 5/2001 | Greene et al. |
| 6,290,674 B1 | 9/2001 | Roue et al. |
| 6,328,727 B1 | 12/2001 | Frazier et al. |
| 6,355,051 B1 | 3/2002 | Sisskind et al. |
| 6,371,971 B1 | 4/2002 | Tsugita et al. |
| 6,398,760 B1 | 6/2002 | Danby |
| 6,419,669 B1 | 7/2002 | Frazier et al. |
| 6,436,088 B2 | 8/2002 | Frazier et al. |
| 6,458,100 B2 | 10/2002 | Roue et al. |
| 6,488,689 B1 | 12/2002 | Kaplan et al. |
| 6,530,934 B1 | 3/2003 | Jacobsen et al. |
| 6,551,303 B1 | 4/2003 | Van Tassel et al. |
| 6,551,341 B2 | 4/2003 | Boylan et al. |
| 6,561,969 B2 | 5/2003 | Frazier et al. |
| 6,585,754 B2 | 7/2003 | Wallace et al. |
| 6,650,923 B1 | 11/2003 | Lesh et al. |
| 6,651,557 B1 | 11/2003 | Frazier et al. |
| 6,652,555 B1 | 11/2003 | Van Tassel et al. |
| 6,652,556 B1 | 11/2003 | Van Tassel et al. |
| 6,666,861 B1 | 12/2003 | Grabek |
| 6,689,150 B1 | 2/2004 | Van Tassel et al. |
| 6,702,825 B2 | 3/2004 | Frazier et al. |
| 6,706,065 B2 | 3/2004 | Langberg et al. |
| 6,712,804 B2 | 3/2004 | Roue et al. |
| 6,730,108 B2 | 5/2004 | Van Tassel et al. |
| 6,746,472 B2 | 6/2004 | Frazier et al. |
| 6,790,229 B1 | 9/2004 | Berreklouw |
| 6,949,113 B2 | 9/2005 | Van Tassel et al. |
| 6,979,344 B2 | 12/2005 | Jones et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,025,756 B2 | 4/2006 | Frazier et al. |
| 7,044,134 B2 | 5/2006 | Khairkhahan et al. |
| 7,056,294 B2 | 6/2006 | Khairkhahan et al. |
| 7,115,110 B2 | 10/2006 | Frazier et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,226,458 B2 | 6/2007 | Kaplan et al. |
| 7,293,562 B2 | 11/2007 | Malecki et al. |
| 7,597,704 B2 | 10/2009 | Frazier et al. |
| 7,608,091 B2 | 10/2009 | Goldfarb et al. |
| 7,717,937 B2 | 5/2010 | Wahr et al. |
| 7,727,189 B2 | 6/2010 | VanTassel et al. |
| 7,780,645 B2 | 8/2010 | Jones |
| 7,842,054 B2 | 11/2010 | Greene, Jr. et al. |
| 8,142,470 B2 | 3/2012 | Quinn et al. |
| 8,636,764 B2 | 1/2014 | Miles et al. |
| 8,690,911 B2 | 4/2014 | Miles et al. |
| 8,715,318 B2 | 5/2014 | Miles et al. |
| 8,740,934 B2 | 6/2014 | McGuckin, Jr. |
| 8,795,328 B2 | 8/2014 | Miles et al. |
| 8,840,641 B2 | 9/2014 | Miles et al. |
| 8,845,711 B2 | 9/2014 | Miles et al. |
| 9,351,716 B2 | 5/2016 | Miles et al. |
| 9,649,115 B2 | 5/2017 | Edmiston et al. |
| 9,693,780 B2 | 7/2017 | Miles et al. |
| 9,693,781 B2 | 7/2017 | Miles et al. |
| 9,883,864 B2 | 2/2018 | Miles et al. |
| 2001/0003161 A1 | 6/2001 | Vardi et al. |
| 2001/0037129 A1 | 11/2001 | Thill |
| 2001/0037141 A1 | 11/2001 | Yee et al. |
| 2002/0022860 A1 | 2/2002 | Borillo et al. |
| 2002/0026094 A1 | 2/2002 | Roth |
| 2002/0026217 A1 | 2/2002 | Baker et al. |
| 2002/0035374 A1 | 3/2002 | Borillo et al. |
| 2002/0062130 A1 | 5/2002 | Jugenheimer et al. |
| 2002/0111647 A1 | 8/2002 | Khairkhahan et al. |
| 2002/0177855 A1 | 11/2002 | Greene, Jr. et al. |
| 2002/0183787 A1 | 12/2002 | Wahr et al. |
| 2002/0183826 A1 | 12/2002 | Dorn et al. |
| 2003/0014075 A1 | 1/2003 | Rosehbluth et al. |
| 2003/0023266 A1 | 1/2003 | Borillo et al. |
| 2003/0050658 A1 | 3/2003 | Trask et al. |
| 2003/0055455 A1 | 3/2003 | Yang et al. |
| 2003/0057156 A1 | 3/2003 | Peterson et al. |
| 2003/0120337 A1 | 6/2003 | Van Tassel et al. |
| 2003/0125790 A1 | 7/2003 | Fastovsky et al. |
| 2003/0153935 A1 | 8/2003 | Mialhe |
| 2003/0171739 A1 | 9/2003 | Murphy et al. |
| 2003/0181942 A1 | 9/2003 | Sutton et al. |
| 2003/0187474 A1 | 10/2003 | Keegan et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208227 A1 | 11/2003 | Thomas |
| 2003/0212432 A1 | 11/2003 | Khairkhahan et al. |
| 2003/0220667 A1 | 11/2003 | van der Burg et al. |
| 2004/0034366 A1 | 2/2004 | van der Burg et al. |
| 2004/0049224 A1 | 3/2004 | Buehlmann et al. |
| 2004/0098028 A1 | 5/2004 | Martinez |
| 2004/0098031 A1 | 5/2004 | van der Burg et al. |
| 2004/0122467 A1 | 6/2004 | Van Tassel et al. |
| 2004/0127935 A1 | 7/2004 | Van Tassel et al. |
| 2004/0153120 A1 | 8/2004 | Seifert et al. |
| 2004/0181237 A1 | 9/2004 | Forde et al. |
| 2004/0215230 A1 | 10/2004 | Frazier et al. |
| 2004/0254594 A1 | 12/2004 | Alfaro |
| 2004/0260317 A1 | 12/2004 | Bloom et al. |
| 2004/0267191 A1 | 12/2004 | Gifford, III et al. |
| 2005/0004652 A1 | 1/2005 | Van Der Burg et al. |
| 2005/0033409 A1 | 2/2005 | Burke et al. |
| 2005/0038470 A1 | 2/2005 | van der Burg et al. |
| 2005/0043759 A1 | 2/2005 | Chanduszko |
| 2005/0049573 A1 | 3/2005 | Van Tassel et al. |
| 2005/0049681 A1 | 3/2005 | Greenhalgh et al. |
| 2005/0060017 A1 | 3/2005 | Fishell et al. |
| 2005/0065589 A1 | 3/2005 | Schneider et al. |
| 2005/0075665 A1 | 4/2005 | Brenzel et al. |
| 2005/0085843 A1 | 4/2005 | Opolski et al. |
| 2005/0090860 A1 | 4/2005 | Paprocki |
| 2005/0113861 A1 | 5/2005 | Corcoran et al. |
| 2005/0149173 A1 | 7/2005 | Hunter et al. |
| 2005/0177182 A1 | 8/2005 | van der Burg et al. |
| 2005/0192616 A1 | 9/2005 | Callister et al. |
| 2005/0192627 A1 | 9/2005 | Whisenant et al. |
| 2005/0222533 A1 | 10/2005 | Chanduszko et al. |
| 2005/0234540 A1 | 10/2005 | Peavey et al. |
| 2005/0234543 A1 | 10/2005 | Glaser et al. |
| 2005/0251144 A1 | 11/2005 | Wilson et al. |
| 2005/0256532 A1 | 11/2005 | Nayak et al. |
| 2005/0267524 A1 | 12/2005 | Chanduszko |
| 2005/0288706 A1 | 12/2005 | Widomski et al. |
| 2006/0000443 A1 | 1/2006 | Kado et al. |
| 2006/0004433 A1 | 1/2006 | Greenberg et al. |
| 2006/0009798 A1 | 1/2006 | Callister |
| 2006/0009800 A1 | 1/2006 | Christianson et al. |
| 2006/0020327 A1 | 1/2006 | Lashinski et al. |
| 2006/0036282 A1 | 2/2006 | Wahr et al. |
| 2006/0052816 A1 | 3/2006 | Bates et al. |
| 2006/0122646 A1 | 6/2006 | Corcoran et al. |
| 2006/0149299 A1 | 7/2006 | Greene et al. |
| 2006/0149307 A1 | 7/2006 | Durgin |

(56) References Cited

U.S. PATENT DOCUMENTS

| | | |
|---|---|---|
| 2006/0149314 A1 | 7/2006 | Borillo et al. |
| 2006/0155323 A1 | 7/2006 | Porter et al. |
| 2006/0206148 A1 | 9/2006 | Khairkhahan et al. |
| 2006/0210816 A1 | 9/2006 | Finley |
| 2006/0217761 A1 | 9/2006 | Opolski |
| 2006/0229668 A1 | 10/2006 | Prestezog et al. |
| 2006/0276839 A1 | 12/2006 | McGuckin, Jr. |
| 2007/0027456 A1 | 2/2007 | Gartner et al. |
| 2007/0066993 A1 | 3/2007 | Kreidler |
| 2007/0073247 A1 | 3/2007 | Ewaschuk |
| 2007/0083230 A1 | 4/2007 | Javois |
| 2007/0083232 A1 | 4/2007 | Lee |
| 2007/0088388 A1 | 4/2007 | Opolski et al. |
| 2007/0112382 A1 | 5/2007 | Thill et al. |
| 2007/0123934 A1 | 5/2007 | Whisenant et al. |
| 2007/0129753 A1 | 6/2007 | Quinn et al. |
| 2007/0129757 A1 | 6/2007 | Armstrong |
| 2007/0135826 A1 | 6/2007 | Zaver et al. |
| 2007/0149995 A1 | 6/2007 | Quinn et al. |
| 2007/0167981 A1 | 7/2007 | Opolski et al. |
| 2007/0173885 A1 | 7/2007 | Cartier et al. |
| 2007/0179527 A1 | 8/2007 | Eskuri et al. |
| 2007/0179583 A1 | 8/2007 | Goetzinger et al. |
| 2007/0191884 A1 | 8/2007 | Eskridge et al. |
| 2007/0198059 A1 | 8/2007 | Patel et al. |
| 2007/0213766 A1 | 9/2007 | Ravikumar |
| 2007/0237720 A1 | 10/2007 | Padilla et al. |
| 2007/0270891 A1 | 11/2007 | McGuckin |
| 2007/0276415 A1 | 11/2007 | Kladakis et al. |
| 2008/0039743 A1 | 2/2008 | Fox et al. |
| 2008/0039929 A1 | 2/2008 | Davis et al. |
| 2008/0119891 A1 | 5/2008 | Miles et al. |
| 2008/0215086 A1 | 9/2008 | Olsen et al. |
| 2008/0249562 A1 | 10/2008 | Cahill |
| 2008/0288042 A1 | 11/2008 | Purdy et al. |
| 2009/0025820 A1 | 1/2009 | Adams |
| 2009/0069840 A1 | 3/2009 | Hallisey |
| 2009/0099596 A1 | 4/2009 | McGuckin, Jr. et al. |
| 2009/0105747 A1 | 4/2009 | Chanduszko et al. |
| 2009/0112050 A1 | 4/2009 | Farnan et al. |
| 2009/0112249 A1 | 4/2009 | Miles et al. |
| 2009/0171386 A1 | 7/2009 | Amplatz et al. |
| 2009/0177163 A1 | 7/2009 | King et al. |
| 2009/0182405 A1 | 7/2009 | Arnault De La Menardiere et al. |
| 2009/0192518 A1 | 7/2009 | Golden et al. |
| 2009/0228038 A1 | 9/2009 | Amin |
| 2009/0299338 A1 | 12/2009 | di Palma |
| 2009/0318948 A1 | 12/2009 | Linder et al. |
| 2010/0191279 A1 | 7/2010 | Kassab et al. |
| 2010/0228279 A1 | 9/2010 | Miles et al. |
| 2010/0228285 A1 | 9/2010 | Miles et al. |
| 2010/0234878 A1 | 9/2010 | Hruska et al. |
| 2010/0324585 A1 | 12/2010 | Miles et al. |
| 2010/0324586 A1 | 12/2010 | Mlles et al. |
| 2010/0324587 A1 | 12/2010 | Miles et al. |
| 2010/0324588 A1 | 12/2010 | Miles et al. |
| 2011/0022079 A1 | 1/2011 | Miles et al. |
| 2011/0046658 A1 | 2/2011 | Connor et al. |
| 2011/0054515 A1 | 3/2011 | Bridgeman et al. |
| 2011/0087272 A1* | 4/2011 | Sargeant ............... A61L 31/14 606/213 |
| 2011/0208233 A1 | 8/2011 | McGuckin, Jr. et al. |
| 2012/0316584 A1 | 12/2012 | Miles et al. |
| 2012/0323267 A1* | 12/2012 | Ren ................. A61B 17/12172 606/191 |
| 2012/0323270 A1* | 12/2012 | Lee ................. A61B 17/12022 606/213 |
| 2013/0138138 A1 | 5/2013 | Clark et al. |
| 2013/0237908 A1* | 9/2013 | Clark ............... A61B 17/12181 604/96.01 |
| 2014/0135817 A1 | 5/2014 | Tischler et al. |
| 2014/0142617 A1 | 5/2014 | Larsen et al. |
| 2014/0257374 A1* | 9/2014 | Heisei ............... A61B 17/0057 606/213 |
| 2015/0066074 A1* | 3/2015 | Miles ................. A61B 17/1214 606/200 |
| 2015/0196305 A1* | 7/2015 | Meyer ............. A61B 17/12181 606/194 |
| 2016/0278784 A1 | 9/2016 | Edmiston et al. |
| 2017/0156840 A1 | 6/2017 | Edmiston et al. |
| 2018/0369594 A1* | 12/2018 | Werneth ........... A61B 17/0057 |

FOREIGN PATENT DOCUMENTS

| | | |
|---|---|---|
| EP | 1266630 | 12/2002 |
| EP | 1358850 | 11/2003 |
| EP | 1523957 | 4/2005 |
| EP | 1741393 | 1/2007 |
| EP | 1768604 | 4/2007 |
| EP | 1659988 | 2/2010 |
| JP | 2008536620 | 9/2008 |
| JP | 2010500917 | 1/2010 |
| WO | 1999/33402 | 7/1999 |
| WO | 00/27292 | 5/2000 |
| WO | 0130266 | 5/2001 |
| WO | 2001/93920 | 12/2001 |
| WO | 2002/071977 | 9/2002 |
| WO | 2003/028802 | 4/2003 |
| WO | 2004045393 | 6/2004 |
| WO | 2004/100803 | 11/2004 |
| WO | 2005053547 | 6/2005 |
| WO | 2005099365 | 10/2005 |
| WO | 2006/033641 | 3/2006 |
| WO | 2006047748 | 5/2006 |
| WO | 2007/054116 | 5/2007 |
| WO | 2007/147145 | 12/2007 |
| WO | WO 2008150346 | 12/2008 |
| WO | 2010/081033 | 7/2010 |
| WO | 2010/148246 | 12/2010 |
| WO | WO 2014078078 | 5/2014 |

OTHER PUBLICATIONS

Supplemental European Search Report dated Jan. 3, 2019 for EP App. No. 18185291.4 (6 pages).

Extended European Search Report dated Jun. 16, 2020 for EP App. No. 20160043.4 (10 pages).

Office Action and English Translation issued in CN Patent App. No. 201610236526.9 dated Sep. 3, 2020 (9 Pages).

English Abstract and English machine translation of the Specification and Claims of DE 102006056283. May 6, 2008.

Office Action and English Translation issued in JP2012-516313 dated Mar. 25, 2014.

International Search Report dated Feb. 7, 2013 for International Application No. PCT/US2012/063074 (5 pages).

International Search Report dated Apr. 26, 2010 for International Application No. PCT/US2010/020549 (7 pages).

International Search Report dated May 7, 2010 for International Application No. PCT/US2010/020547 (4 pages).

International Search Report dated May 6, 2010 for International Application No. PCT/US2010/020539 (5 pages).

International Search Report dated Jun. 15, 2009 for International Application No. PCT/US2008/080374 (7 pages).

Extended European Search Report dated Aug. 17, 2020 for EP App. No. 20162101.8 (7 pages).

* cited by examiner

MEDICAL DEVICE AND SYSTEM FOR OCCLUDING A TISSUE OPENING AND METHOD THEREOF

TECHNICAL FIELD

The present invention relates generally to the occlusion of tissue openings or appendages and, more specifically, to devices, systems and methods for occluding or otherwise structurally altering such openings and appendages including, for example, left atrial appendages.

BACKGROUND

The upper chambers of the heart, the atria, have appendages attached to each of them. For example, the left atrial appendage is a feature of all human hearts. The physiologic function of such appendages is not completely understood, but they do act as a filling reservoir during the normal pumping of the heart. The appendages typically protrude from the atria and cover an external portion of the atria. Atrial appendages differ substantially from one to another. For example, one atrial appendage may be configured as a tapered protrusion while another atrial appendage may be configured as a re-entrant, sock-like hole. The inner surface of an appendage is conventionally trabeculated with cords of muscular cardiac tissue traversing its surface with one or multiple lobes.

The atrial appendages appear to be inert while blood is being pumped through them during normal heart function. In other words, the appendages do not appear to have a noticeable effect on blood pumped through them during normal heart function. However, in cases of atrial fibrillation, when the atria go into arrhythmia, blood may pool and thrombose inside of the appendages. Among other things, this can pose a stroke risk when it occurs in the left appendage since the thrombus may be pumped out of the heart and into the cranial circulation once normal sinus rhythm is restored following arrhythmia events.

Historically, appendages have sometimes been modified surgically to reduce the risk imposed by atrial fibrillation. In recent years devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This process, coupled with the growth of endothelium over the face of the device, can leave a smooth, endothelialized surface where the appendage is located. In comparison to surgical procedures, devices implanted percutaneously are a less invasive means for addressing the problems associated with the left atrial appendage.

However, due to the wide variability of the ostium size and volume of the left atrial appendage, current implantable devices conventionally include a structure that cannot meet such variability, resulting in inadequate devices for many left atrial appendage anatomies. Further, such implantable devices are substantially limited by the orientation by which they can successfully be deployed. Even further, another problem with many of the current implantable devices is that they are anchored with hooks of a size and length that often results in perfusion risk to the patient. As such, it would be advantageous to provide a percutaneous system, method and/or device that addresses, for example, the issues of perfusion risk, implant orientation, the variability in sizes and shapes of the left atrial appendage, or all of these, in order to provide high success in left atrial appendage modification.

A variety of features and advantages will be apparent to those of ordinary skill in the art upon reading the description of various embodiments set forth below.

BRIEF SUMMARY OF THE INVENTION

Embodiments of the present invention are directed to various devices, systems and methods of occluding an opening in the tissue of a body. For example, in one embodiment, a medical device for occluding a left atrial appendage of a heart is provided. The medical device includes a cover portion and a foam anchor portion. The cover portion includes a hub and a cover, the cover extending radially from the hub such that the cover portion is sized and configured to be positioned along a proximal side of an ostium of the left atrial appendage. The foam anchor portion is coupled to the cover portion with a flexible member. The foam anchor portion extends between a proximal end and a distal end to define a length and an axis, the axis defined along the length of the foam anchor portion. The foam anchor portion defines a curved external surface radially extending relative to the axis such that the curved external surface extends between the proximal and distal ends of the foam anchor portion. Further, the foam anchor portion is configured to self-expand to provide an outward biasing force from the curved external surface such that a circumferential surface area of the curved external surface biases against tissue of the left atrial appendage.

In another embodiment, the curved external surface defines a total surface area, and wherein at least half of the total surface area of the curved external surface is sized and configured to grab and contact tissue within the left atrial appendage. In another embodiment, the curved external surface of the foam anchor portion includes micro protrusions sized and configured to grab and contact tissue within the left atrial appendage with the outward biasing force.

In another embodiment, the curved external surface of the foam anchor portion includes a raised grid pattern sized and configured to grab tissue with the outward biasing force. In yet another embodiment, the curved external surface of the foam anchor portion defines multiple protrusions sized and configured to grab and anchor to tissue with the outward biasing force. In still another embodiment, the curved external surface of the foam anchor portion defines multiple recesses therein, the multiple recesses defined by raised portions of the curved external surface of the foam anchor portion. In another embodiment, the curved external surface of the foam anchor portion defines multiple ring shaped structures.

In another embodiment, the foam anchor portion expands to a shape resembling at least one of a truncated cone structure and a cylindrical structure. In still another embodiment, the foam anchor portion extends with a variable foam density between a proximal end portion and a distal end portion of the foam anchor portion, the distal end portion having a greater foam density than the proximal end portion. In another embodiment, the foam anchor portion includes variable expandability between a proximal end portion and a distal end portion of the foam anchor portion, the distal end portion having greater expandability than the proximal end portion.

In another embodiment, the cover portion extends with a proximal facing surface having a concave structure, the proximal facing surface facing away from a distal end of the medical device. In another embodiment, wherein, upon the cover portion and the foam anchor portion being deployed, the flexible member is extendable at an angle relative to the axis of the foam anchor member.

In accordance with another embodiment of the present invention, a medical device system for occluding a left atrial appendage of a heart is provided. The medical device system includes a delivery device and a medical device. The delivery device includes a handle and a catheter extending between a proximal end and a distal end, the proximal end coupled to the handle, the catheter defining a lumen extending longitudinally through the catheter between the proximal and distal ends of the catheter. The medical device is operatively coupled to the handle. Further, the medical device is sized and configured to be moved between a constricted state and an expanded state such that, in the constricted state, the medical device is within a distal end portion of the catheter and, in the expanded state, the medical device is advanced from the catheter. The medical device includes a cover portion and a foam anchor portion. The cover portion includes a hub and a cover, the cover extending radially from the hub. The cover portion is sized and configured to be positioned along a proximal side of an ostium of the left atrial appendage. The foam anchor portion is coupled to the cover portion with a flexible member. Further, the foam anchor portion extends between a proximal end and a distal end to define a length and an axis, the axis defined along the length of the foam anchor portion. The foam anchor portion defines a curved external surface radially extending relative to the axis such that the curved external surface extends between the proximal and distal ends of the foam anchor portion. The foam anchor portion is configured to self-expand to provide an outward biasing force along the curved external surface such that a circumferential surface area of the curved external surface biases against tissue of the left atrial appendage.

In another embodiment, the curved external surface defines a total surface area, and wherein at least half of the surface area of the curved external surface is sized and configured to grab and contact tissue within the left atrial appendage with the outward biasing force. In another embodiment, the curved external surface of the foam anchor portion includes micro protrusions sized and configured to grab and contact tissue within the left atrial appendage with the outward biasing force. In another embodiment, wherein, upon the cover portion and the foam anchor portion being deployed, the flexible member is extendable at an angle relative to the axis of the foam anchor member.

In accordance with another embodiment of the present invention, a method for occluding a left atrial appendage a heart is provided. The method steps include: advancing a medical device with a catheter of a delivery system through a vasculature and into the left atrial appendage of the heart, the medical device positioned in a constricted state in a distal end portion of the catheter, the medical device including a cover portion and a foam anchor portion with a flexible member coupled therebetween, the foam anchor portion having a length extending between a proximal end and a distal end and the foam anchor portion defining an axis extending axially along the length; deploying the anchor portion of the medical device from the distal end portion of the catheter to self-expand so that a circumferential surface area of a curved external surface of the foam anchor portion contacts and lodges against tissue within the left atrial appendage with an outward biasing force; deploying the cover portion of the medical device from the distal end portion of the catheter so that the cover portion self-expands to an expanded state; and cinching the cover portion of the medical device against an ostium of the left atrial appendage to shorten a length of the flexible member coupled between the foam anchor portion and the cover portion.

In another embodiment, the method step of cinching includes tautly extending the flexible member from the foam anchor portion so that the flexible member extends at an angle relative to the axis of the foam anchor portion. In another embodiment, the method step of deploying the anchor portion includes anchoring the foam anchor portion with the circumferential banded area of the curved external surface and with micro protrusions defined along the curved external surface of the foam anchor portion. In still another embodiment, the method step of deploying the cover portion includes expanding the cover portion with spokes extending radially from a hub of the cover portion. In another embodiment, the method further includes releasing the catheter from the medical device and withdrawing the delivery system from the heart to permanently leave the medical device in the left atrial appendage.

In accordance with another embodiment of the present invention, a medical device for occluding a left atrial appendage of a heart is provided. The medical device includes a foam anchor extending between a proximal end and a distal end to define a length and an axis defined along the length of the foam anchor, the foam anchor defining a curved external surface radially extending relative to the axis such that the curved external surface extends between the proximal and distal ends of the foam anchor, the foam anchor configured to self-expand to provide an outward biasing force from the curved external surface such that a circumferential surface area of the curved external surface biases against tissue of the left atrial appendage.

In another embodiment, the foam anchor extends between the proximal and distal ends to exhibit at least one of a truncated cone structure and a cylindrical structure. In another embodiment, the curved external surface defines a total surface area, and wherein at least half of the total surface area of the curved external surface is sized and configured to grab and contact tissue within the left atrial appendage. In another embodiment, the curved external surface of the foam anchor portion includes micro protrusions sized and configured to grab and contact tissue within the left atrial appendage with the outward biasing force.

In another embodiment, the curved external surface of the foam anchor portion includes a raised grid pattern sized and configured to grab tissue with the outward biasing force. In yet another embodiment, the curved external surface of the foam anchor portion defines multiple protrusions sized and configured to grab and anchor to tissue with the outward biasing force. In still another embodiment, the curved external surface of the foam anchor portion defines multiple recesses therein, the multiple recesses defined by raised portions of the curved external surface of the foam anchor portion. In another embodiment, the curved external surface of the foam anchor portion defines multiple ring shaped structures.

In still another embodiment, the foam anchor portion extends with a variable foam density between a proximal end portion and a distal end portion of the foam anchor portion, the distal end portion having a greater foam density than the proximal end portion. In another embodiment, the foam anchor portion includes variable expandability between a proximal end portion and a distal end portion of the foam anchor portion, the distal end portion having greater expandability than the proximal end portion.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
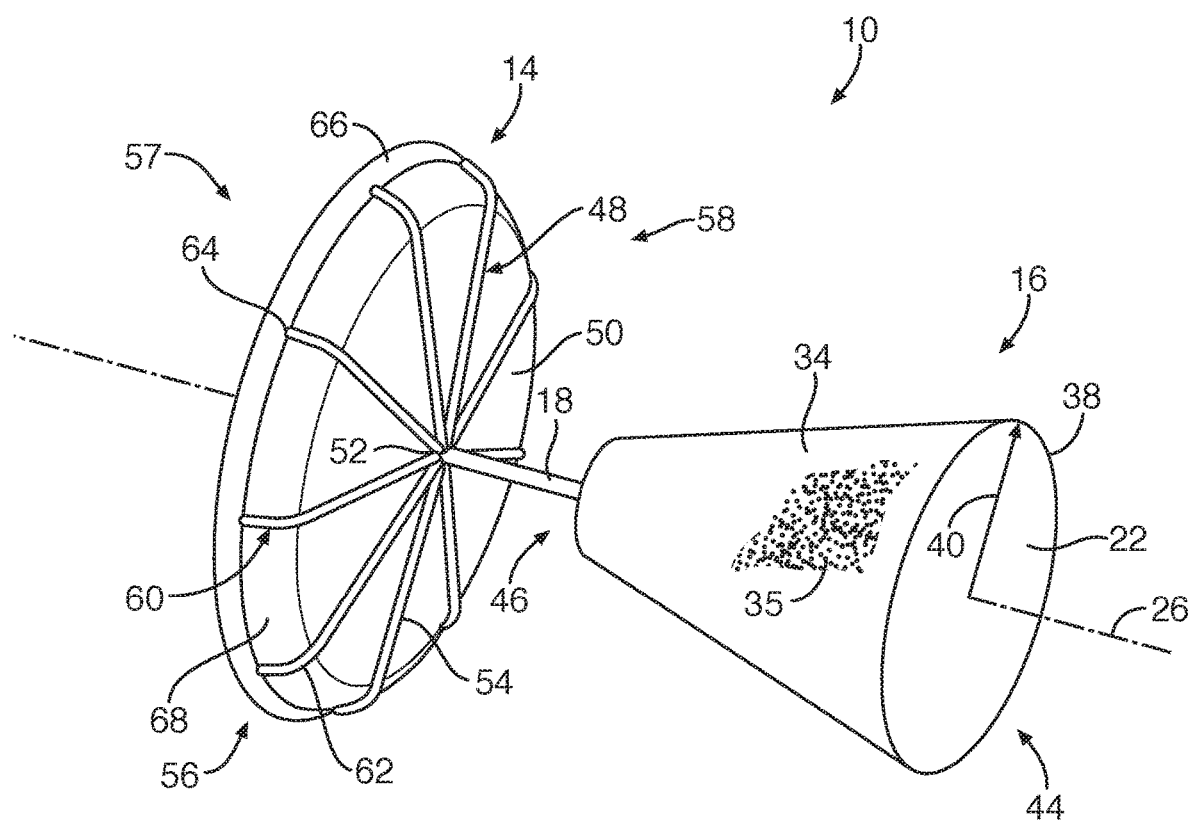
FIG. 1 is a perspective rear view of a medical device, according to one embodiment of the present invention.
Figure 2:
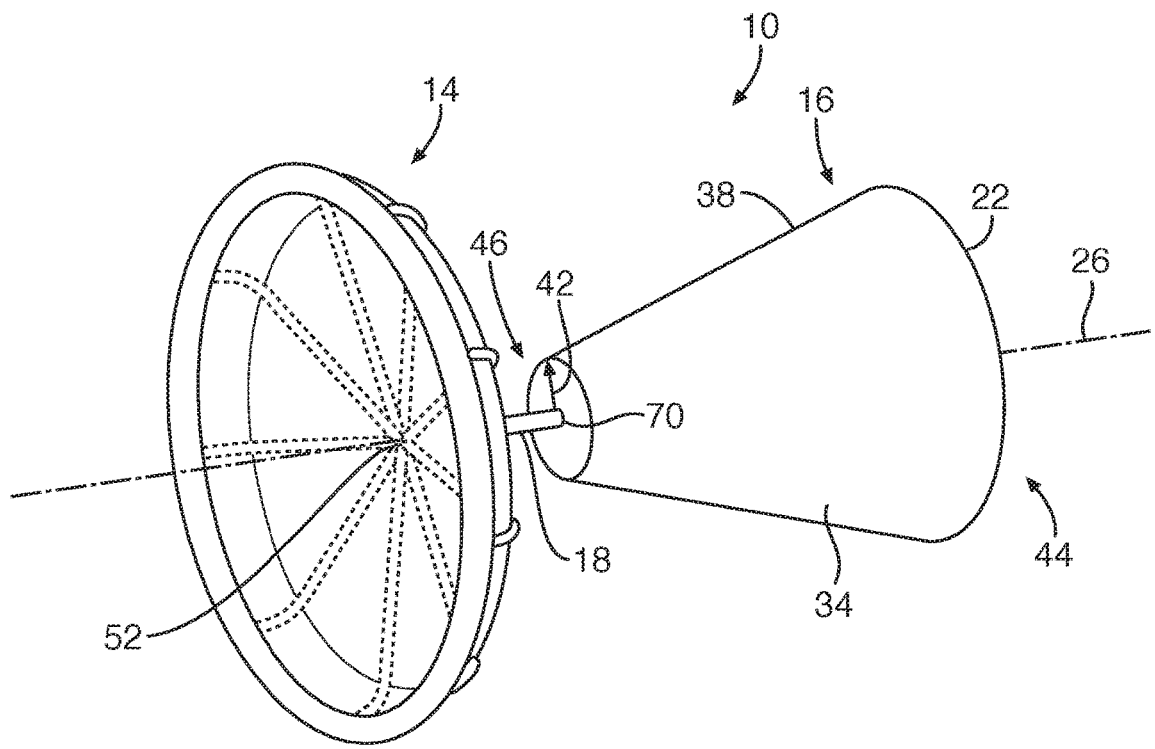
FIG. 2 is a perspective front view of the medical device, according to another embodiment of the present invention.
Figure 3:
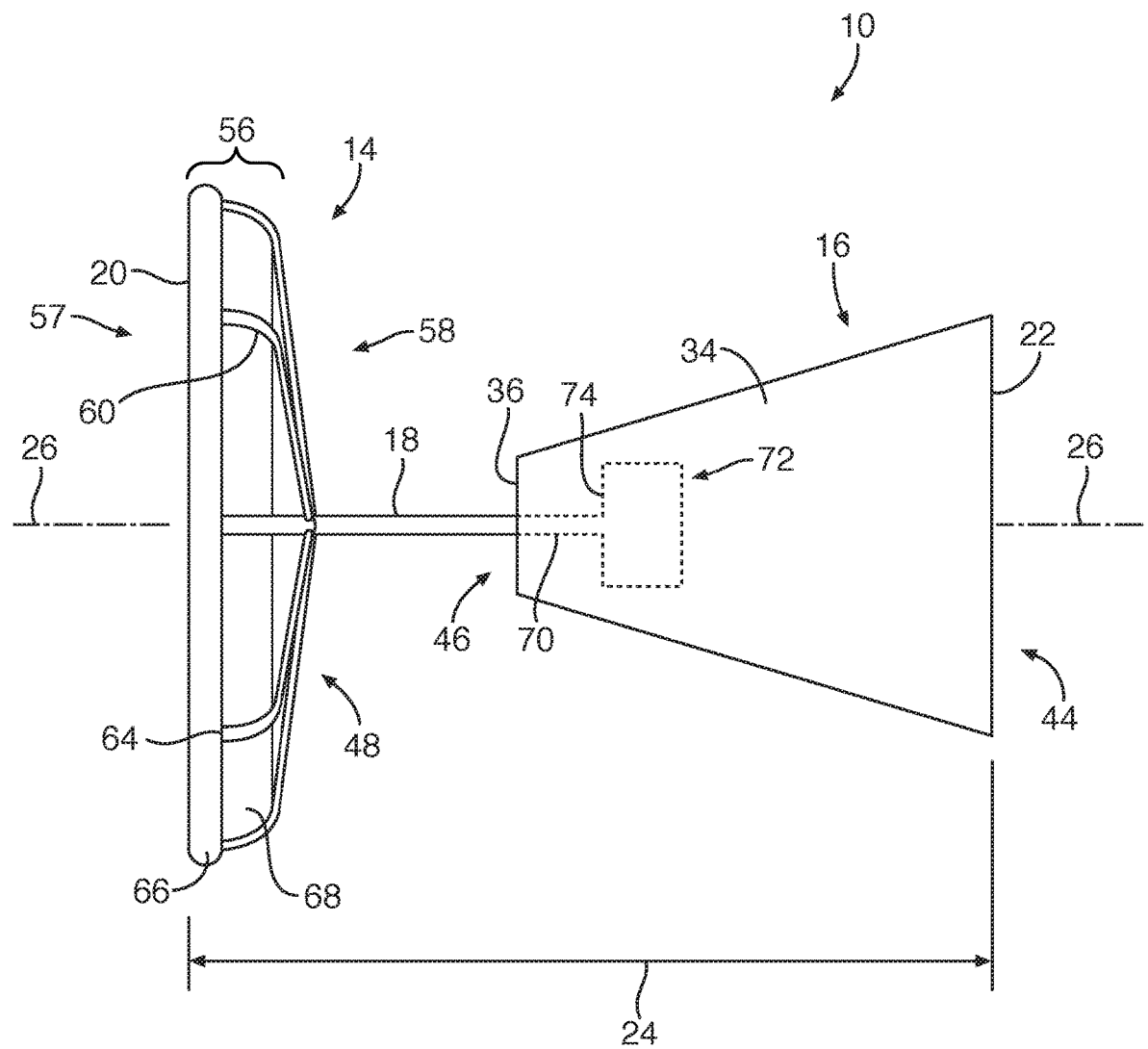
FIG. 3 is a side view of the medical device, according to another embodiment of the present invention.

Referring to FIGS. 1, 2 and 3, a medical device 10 sized and configured to be percutaneously delivered with a delivery system 80 (FIG. 4) through the cardiovascular system is provided. The medical device 10 and the delivery system 80 may be employed in interventional procedures for closing or occluding an opening or cavity such as, for example, a left atrial appendage ("LAA") within a heart (not shown). In one embodiment, the medical device may include a cover portion 14 and an anchor portion 16 with a flexible member 18 coupled therebetween. The anchor portion 16 of the medical device 10 may be sized to self-expand so as to lodge within the left atrial appendage in an atraumatic manner without hooks or tines to minimize perfusions that may otherwise occur from anchoring in the left atrial appendage. Such atraumatic anchoring of the medical device 10 may be employed with an outward biasing force of the anchor portion 16 such that an external surface 34 of the anchor portion, along opposing external surfaces 34 of the anchor portion 16, maintains contact with tissue within the left atrial appendage. In this manner, the body and external surface 34 of the anchor portion 16 of the medical device 10 may be sized to provide a self-expanding and biasing force 17 (FIG. 7) to lodge itself atraumatically against tissue within the left atrial appendage.

As previously set forth, the medical device 10 may include the cover portion 14 and the anchor portion 16 with the flexible member 18 extending therebetween. The medical device 10 may extend between a proximal end 20 and a distal end 22 along a length 24 of the medical device 10 and may define an axis 26 extending longitudinally through the medical device and through each of the cover portion 14 and anchor portion 16 along the length 24 of the medical device 10. The medical device 10 may include structural components that self-expand from a constricted state within, for example, a distal end portion 84 of a catheter 82 (see FIGS. 4 and 5) to an expanded state (e.g., FIG. 1).

For example, in one embodiment, the anchor portion 16 may be formed from a foam material extending between an anchor proximal end 36 and the distal end 22 of the medical device 10. In the expanded state, the foam material may be sized to extend in a trapezoidal cylinder or truncated cone structure or the like. Such structure may be oriented so that the anchor portion 16 extends radially larger toward the distal end 22. Further, along the length of the anchor portion 16, the external surface 34 of the anchor portion 16 may extend radially or with a curved or arcuate surface relative to the axis 26 between the anchor proximal end 36 and the distal end 22. In one embodiment, the distal end 22 of the anchor portion 16 may be a generally flat surface extending to a circular periphery 38 so as to define a distal end radius 40 relative to the longitudinal axis 26. Similarly, the anchor proximal end 36 may be a generally flat surface extending to a circular periphery to define a proximal end radius 42 relative to the longitudinal axis 26. In another embodiment, a distal side surface 44 and/or a proximal side surface 46 of the anchor portion 16 may extend with a convex surface or concave surface extending radially relative to the longitudinal axis 26.

As previously set forth, the anchor portion 16 may be formed from a foam material. The foam may be of a structural characteristic that can be constricted and minimized in size such as within the lumen of the catheter 82 (FIG. 4) and, upon being advanced from the catheter 82, the foam may self-expand in an immediate manner. In one embodiment, the foam of the anchor portion 16 may self-expand isotropically. In another embodiment, the foam may self-expand in an anisotropic manner. In another embodiment, the foam may expand with a greater degree toward the distal end 22 of the anchor portion 16 than toward the anchor proximal end 36. In another embodiment, the foam may expand with a greater expanding force along a distal portion of the anchor portion 16 than that of a more proximal portion of the anchor portion 16. In another embodiment, the foam may define pores or a porosity size therein. The porosity size of the foam of the anchor portion 16 may be in the range of about 300 to 600 microns, and preferably about 500 microns.

In still another embodiment, the foam material may be generally homogeneous in density. In another embodiment, the foam material may include a variable density along the length thereof. For example, the variable density may progressively be more dense from the anchor proximal end 36 toward the distal end 22 of the anchor portion 16. In another embodiment, the variable density may progressively be denser from the distal end 22 toward the anchor proximal end 36. In another embodiment, the density of the foam material of the anchor portion 16 may be variable in that portions of the anchor portion 16 may exhibit different densities. Such different densities of the foam material may be, for example, in two parts or three parts of the anchor portion 16. For example, the variable density foam material may be divided with a proximal anchor portion and a distal anchor portion, the distal anchor portion being denser than the proximal anchor portion. In an alternate embodiment, the variable density foam material may be divided with a proximal anchor portion, an intermediate anchor portion, and a distal anchor portion, the intermediate and distal anchor portions being denser than the proximal anchor portion and the distal anchor portion being denser than the intermediate anchor portion. In another embodiment, the proximal portion of the anchor portion 16 may be more dense than the intermediate anchor portion or the distal anchor portion. In this manner, there are multiple embodiments as to the foam material exhibiting a variable density along the length of the anchor portion 16.

Further, in another embodiment, the external surface 34 of the anchor portion 16 and foam material may be non-smooth or somewhat variable and inconsistent such that the external surface 34 may define micro protrusions 35 along a periphery of the external surface 34 such that the micro protrusions 35 may be slightly raised relative to surrounding portions of the external surface 34. In one embodiment, the micro protrusions 35 may be random and an inherent characteristic of the external surface 34 of the foam material such that the micro protrusions 35 may assist in grabbing onto tissue within the left atrial appendage. In another embodiment, the micro protrusions 35 may be formed and spaced a predetermined distance relative to each other over the external surface 34 of the foam. In another embodiment, the micro protrusions 35 may include hardened tips such that the micro protrusions 35 exhibit effective micro tines sized and configured to grab tissue.

The foam material of the anchor portion 16 may be formed from a polymeric foam material. The polymeric foam material may be a polyurethane foam material or any other suitable foam material, such as a polyurethane blend, such as polycaprolactane-zinc-oxide. In another embodiment, the polymeric foam may be hydrophilic. In another embodiment, the foam may be reticulated foam. In another embodiment, the foam may be a non-reticulated foam. In another embodiment, the anchor portion may include other polymeric materials, such as ePTFE and/or silicone.

Further, in another embodiment, the polymeric foam may include multiple markers (not shown) embedded therein. Such markers may be positioned within the foam material to assist the physician to appropriately orient and position the anchor portion 16 in the left atrial appendage by employing imaging techniques, as known in the art. The markers may be made from a radiopaque material, such as platinum, gold, tantalum, or alloys thereof, or any other suitable radiopaque materials that are biocompatible.

The cover portion 14 of the medical device 10 may include a frame structure 48 and a cover 50. The frame structure 48 of the cover portion 14 may include a hub 52, spokes 54 and a lip portion 56. The frame structure 48 may be formed from super elastic materials, such as Nitinol and/or polymeric materials. The spokes 54 may extend radially from the hub 52 to the lip portion 56. The frame structure 48 may support the cover 50 such that the cover 50 may extend along at least a proximal side 57 of the frame structure 48. The cover portion 14 may extend with a disc like structure to define the proximal side 57 and a distal side 58 of the cover portion 14. The proximal side 57 may extend with a concave structure. The distal side 58 may generally extend with a convex structure. Such concave structure of the proximal side 57 of the cover portion 14 may be at least partially formed with the spokes 54 of the frame structure 48. The spokes 54 may extend from the hub 52 so as to extend radially and slightly proximally to spoke end portions 60. At the spoke end portions 60, the spokes 54 may include a bend or curved portion 62 so that the spokes 54 curve to extend more proximally to spoke ends 64. Such spoke end portions 60 and/or curved portions 62 of the spokes 54 may at least partially form the concave structure of the proximal side 57 of the cover portion 14 and, further, the spoke end portions 60 may at least partially form the lip portion 56 of the cover portion 14. The lip portion 56 may define an outer lip 66 and an inner lip 68. The outer lip 66 may extend radially with a ring structure and may be positioned more proximal than the inner lip 68. The inner lip 68 may extend radially and more distal than the outer lip 66 such that the inner lip 68 may extend smaller or with a smaller radius than the outer lip 66 so that an external profile of the outer lip 66 exhibits a distal step inward relative to the outer lip 66 and the axis 26 of the medical device 10. The spoke end portions 60 may extend along an external surface of the inner lip 68 with the spoke ends 64 positioned within or adjacent the outer lip 66 of the lip portion 56. In this manner, the spokes 54 of the frame structure 48 may support the lip portion 56 and the cover 50 of the cover portion 14.

The frame structure 48 of the cover portion 14 may be sized and configured to self-expand from the constricted state to the expanded state. The cover portion 14 may be constricted in the distal end portion 104 of the catheter 82 such that the spokes 54 of the frame structure 48 may fold inward so as to extend and fold proximally from the hub 52. In this position, the spokes 54 may extend generally parallel within the catheter 82. Upon being advanced from the distal end portion 84 of the catheter 82, the spokes 54 may be biased to self-expand to a radially extending expanded position such that the cover portion 14 may expand the lip portion 56 and cover 50. Further, in one embodiment, the spokes 54 may be designed to expand independently relative to each other such that the spokes 54 may not be interconnected to each other, except adjacent the hub 52 and via the cover 50 or lip portion 56. Such independent expansion of the spokes 54 may better facilitate the spokes biasingly conforming to the wide variety of ostium shapes of the left atrial appendage. In another embodiment, the spokes 54 may interconnect with adjacently extending spokes 54 at one or more positions along a length of a given spoke. Such interconnection may keep any one spoke from tangling with another spoke as the cover portion is moved between the expanded and constricted positions, as set forth above.

The cover 50 of the cover portion 14 may be a material sized and configured to induce tissue ingrowth therein and over the cover 50. As previously set forth, the cover 50 may extend at least along the proximal side 57 of the frame structure 48 and cover portion 14. In one embodiment, the cover may me formed of a polymeric type material, such as expanded polytetrafluoroethylene (ePTFE), or any other suitable polymeric material configured to induce tissue growth. For example, the cover 50 may include multiple layers of a polymeric material, such as the ePTFE, such as two to six layers or more. The multiple layers of the cover may be formed by bonding the layers together, such as with adhesives and/or thermal bonding heat processes or other appropriate processes known in the art. Further, the cover 50 may be adhesively attached to the proximal side 57 of the frame structure 48, or the cover 50 may be attached to the frame structure 48 with any other suitable technique or means for attaching to the frame structure 48, such as with heat bonding techniques. In another embodiment, the material of the cover 50 may define pores or porosity therein, the pores sized within the range of about 50 microns to about 200 microns.

Figure 4:
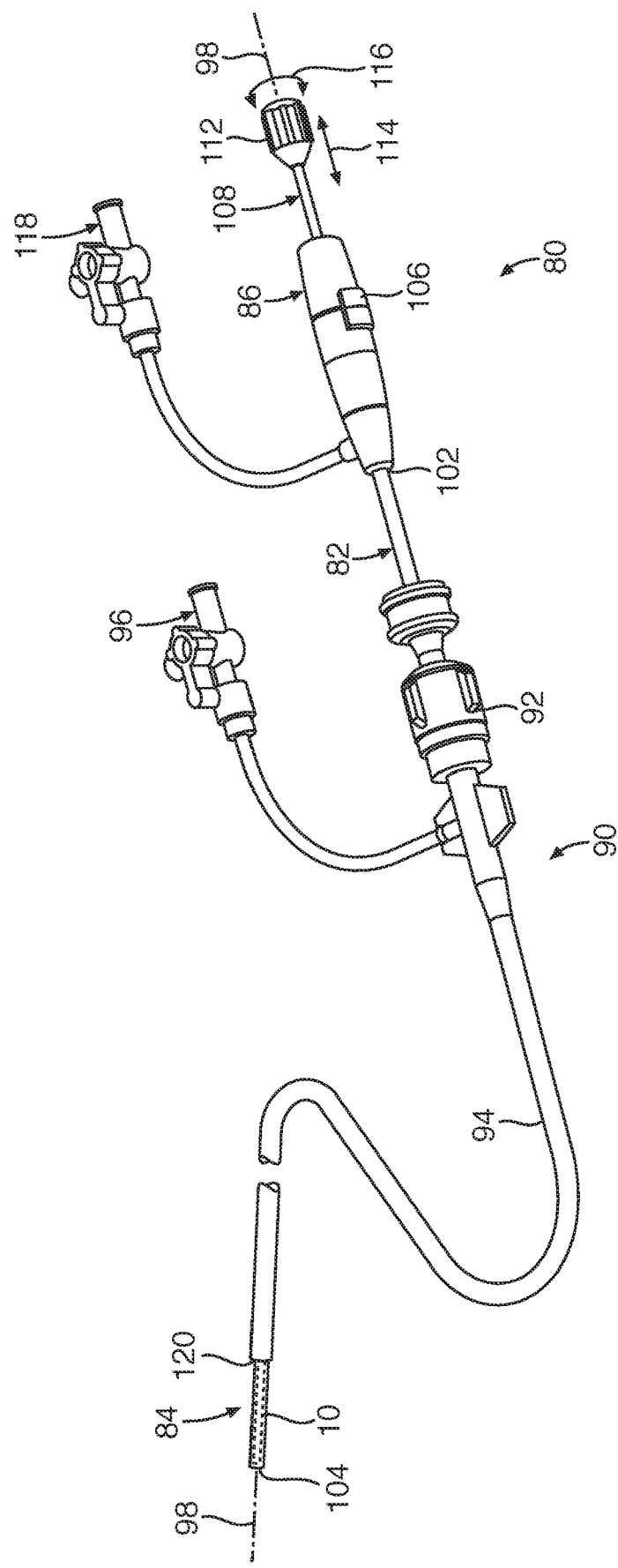
FIG. 4 is a perspective view of a delivery system for the medical device, according to another embodiment of the present invention.

Further, the cover 50 may extend with the spoke end portions 60 to form the inner lip 68 such that the cover 50 may be adhesively attached to spoke end portions 60 to form inner lip 68. The outer lip 66 may be adhesively attached to the inner lip 68 of the cover 50 and may extend radially in the ring like structure so as to be supported with the spoke ends 64 of the frame structure 48 and be contiguous with the cover 50. The outer lip 66 of the lip portion 56 may be a resilient polymeric material, such as foam or ePTFE, or any other suitable polymeric material. In another embodiment, the outer lip 66 may be a continuous extension of the cover 50. With this arrangement, the lip portion 56 may be sized and configured to nest in a soft conforming manner along an outer or front side of a periphery of an ostium of a left atrial appendage. In one embodiment, the lip portion 56 may be biased to self-expand to the ring shaped structure. In another embodiment, the lip portion 56 may expand to the ring shaped structure via the frame structure 48 being moveable and biased to a radially expanded position. Further, the lip portion 56 may be sized and configured to be collapsible in a minimized manner with the entire cover portion to readily fit within the catheter 82 (FIG. 4). Furthermore, similar to the anchor portion 16, the cover portion 14 may include markers. The markers may be positioned along the lip portion 56 and/or the along the spokes 54 of the cover portion 14. Such markers may be formed of radiopaque material, such as platinum, gold, tantalum, or alloys thereof, or any other suitable radiopaque material, so that the physician may readily view the orientation and positioning of the cover portion 14 and the medical device 10 relative to the left atrial appendage by employing various imaging techniques, as known in the art.

As previously set forth, the flexible member 18 may extend between the cover portion 14 and the anchor portion 16 of the medical device 10. The flexible member 18 may be an elongated flexible filament type structure that couples the anchor portion 16 to the cover portion 14 of the medical device 10. In the drawing figures, the flexible member 18 is depicted in a tension state, such that in one embodiment, the flexible member 18 may be of the type that does not provide an appreciable compressive force and, if not in the tension state, the flexible member 18 would move to a limp position. The flexibility of the flexible member 18 may facilitate orienting the cover portion 14 relative to the anchor portion 16 so that the medical device 10 may conform to the particular anatomy of a given left atrial appendage, for example.

In one embodiment, the flexible member 18 may extend between an anchor hub 70 and the hub 52 of the cover portion 14 such that a portion of the flexible member 18 may be coupled to the hub 52 of the cover portion 14. The flexible member 18, in a pre-released position of the medical device 10 relative to the delivery system 80, may continue proximally from the hub 52 and be operatively coupled to the handle 108 of the delivery system 80. At the anchor hub 70, the flexible member 18 may be coupled to the anchor hub 70 such that the anchor hub 70 may include coupling structure 72 for maintaining the anchor hub 70 to the anchor portion 16. Such coupling structure 72 may include extensions 74 extending laterally relative to the axis 26. In another embodiment, the flexible member 18 may include structure extending directly therefrom that may extend within the anchor portion 16 so as to extend laterally relative to the longitudinal axis 26 of the anchor portion 16 to hold the flexible member 18 to the anchor portion 16.

With reference to FIGS. 3 and 4, a delivery system 80 for delivering the medical device 10 (shown in outline in FIG. 4) to, for example, the left atrial appendage is provided. As previously set forth, the medical device 10 may be coupled to the delivery system 82 with the flexible member 18 or another flexible element. In addition, the medical device 10, in the constricted state, may be maintained in the distal end portion 84 of the catheter 82 of the delivery system 80 with an interference type fit. The primary components of the delivery system 80 may include the catheter 82 fixedly coupled to a handle 86. Further, the delivery system 80 may be sized and configured to cooperate with a sheath system 90. The sheath system 90 may be a standard sheath system sized and configured to advance over a guide wire (not shown) through the cardio vascular system. In one embodiment, the sheath system 90 may include a sheath hub 92 and a sheath 94, the sheath hub 92 positioned and coupled to a proximal end of the sheath 94. The sheath system 90 may also include a sheath fluid port 96 sized and configured to feed fluid to a lumen of the sheath 94. Such lumen of the sheath 94 may be sized and configured to receive and advance the catheter 82 of the delivery system 80 therethrough, upon the sheath 94 being advanced to a desired location within the cardio vascular system, such as to the left atrial appendage of the heart.

The catheter 82 may define a lumen extending along a length of the catheter and extending along a catheter longitudinal axis 98 between a proximal end 102 and a distal end 104, the proximal end 102 coupled to the handle 86. The handle 86 may include a switch 106 and a push rod 108, the push rod 108 extending from a proximal end of the handle 86. The push rod 108 may include a knob 112 at a proximal end of the push rod 108 and a distal pusher portion 110 (FIG. 5) at a distal end of the push rod 108. Further, a portion of the push rod 108 may be a tubular coil (not shown) extending within the lumen of the catheter 82 to the distal pusher portion 110 of the push rod 108, the tubular coil defining a lumen sized and configured to hold a portion of the flexible member 18 (FIG. 1). The knob 112 may be fixed to the proximal end of the push rod 108 and may be sized and configured for a physician to readily grasp and move the push rod bi-linearly, as shown by bi-directional arrow 114, and/or the knob 112 may be moveable rotationally, as shown by rotational arrow 116. For example, the push rod 108 may be moved distally for deploying the medical device 10 from the distal end portion 84 of the catheter 82 and the push rod 108 may be moved proximally for re-capturing the medical device 10 into the distal end portion 84 of the catheter 82. Further, the knob 112 may be rotatable for releasing the medical device 10 from the delivery system 80, for example. In another embodiment, the switch 106 may be moved to multiple positions to control displacement of the push rod 108 while, for example, deploying the medical device 10 or re-capturing the medical device 10. In addition, the delivery system 80 may include a fluid port 118 associated with the handle 86 to advance fluid to the lumen of the catheter 82. Further detail and functionality of the various components of the delivery system 80 will be described in conjunction with description of delivering the medical device 10 with the delivery system 80 in the left atrial appendage.

Figure 5:
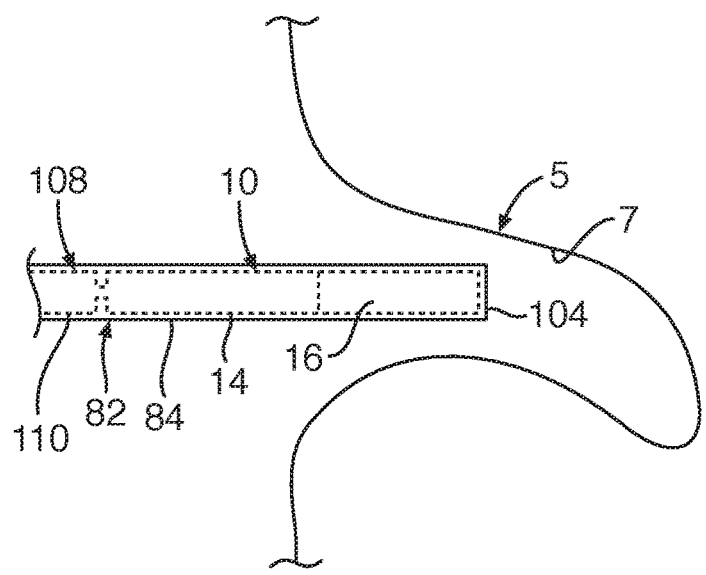
FIG. 5 is a side view of a distal portion of the delivery system, depicting a distal portion of the delivery system adjacent a left atrial appendage of a heart, according to another embodiment of the present invention.

Now with reference to FIGS. 4-11, one embodiment for delivering the medical device 10 with the delivery system 80 to a left atrial appendage 5 of a heart will now be described. With reference to FIGS. 4 and 5, the medical device 10 may be pre-positioned or prepared for positioning within the distal end portion 84 of the catheter 82. Upon the medical device 10 being positioned adjacent the distal end portion 84 of the catheter 82, the physician may make preparations for positioning a distal end 120 of the sheath 94 adjacent the left atrial appendage 5. Such may be employed by using typical interventional techniques with, for example, a guide wire and a sheath, as known in the art. Once the sheath 94 has been appropriately advanced adjacent to the left atrial appendage 5, the catheter 82 of the delivery system 80 may be advanced through the sheath 94 so that the distal end portion 84 of the catheter 82 is positioned adjacent the left atrial appendage 5. Once positioned, the sheath 94 may be fully or slightly withdrawn from the distal end portion 84 of the catheter 82 so that the distal end portion 84 may be positioned within the left atrial appendage 5, as depicted in FIG. 5.

Figure 6:
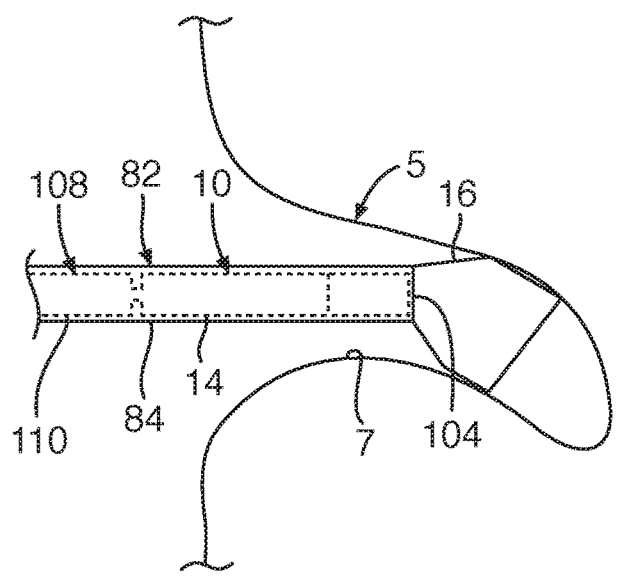
FIG. 6 is a side view of the distal portion of the delivery system, depicting the medical device being partially advanced from the distal portion of the delivery system in the left atrial appendage, according to another embodiment of the present invention.
Figure 7:
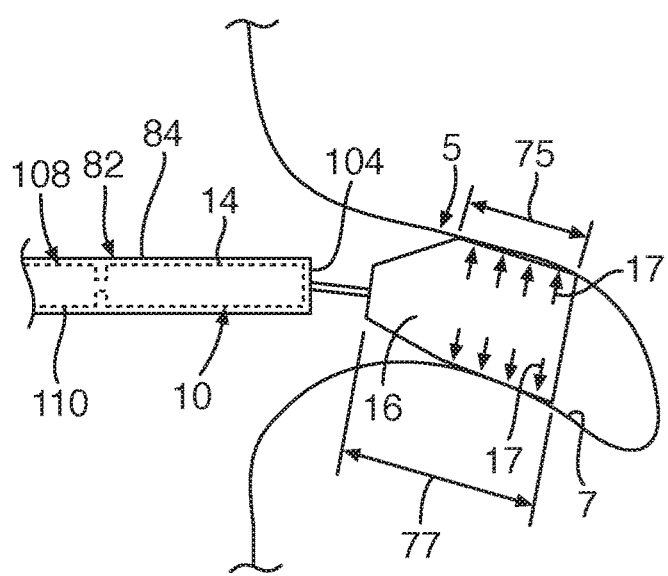
FIG. 7 is a side view of the distal portion of the delivery system, depicting an anchor portion of the medical device in an expanded state in the left atrial appendage, according to another embodiment of the present invention.

With reference to FIGS. 4-7, once the physician is satisfied with the position of the distal end portion 84 of the catheter 82, the physician may advance the anchor portion 16 into the left atrial appendage 5 with the push rod 108 actuatable at the handle 86. The push rod 108 may extend from the knob 112 and continue distally through the handle and the lumen of the catheter 82 to just proximal and adjacent the medical device 10 at the distal end portion 84 of the catheter 82. The physician may move the push rod 108 distally to a first hard stop to deploy the anchor portion 16 of the medical device 10 by moving the knob 112 distally, as shown by bi-directional arrow 114. As the knob 112 and push rod 108 are moved distally, the distal pusher portion 110 of the push member 108 may push the medical device 10 from the distal end 104 of the catheter 82 such that the anchor portion 16 advances from the catheter 82. As the anchor portion 16 proceeds from the catheter 82, the structural characteristics of the anchor portion 16 may effect immediate expansion so as to self-expand, as depicted in FIGS. 6 and 7.

Because the anchor portion may be sized and configured to be larger than the left atrial appendage 5, a majority of the external surface 34 of the anchor portion 16 may self-expand and bias against tissue 7 with an outward biasing force 17 within the left atrial appendage 5 such that opposing surfaces or sides along the periphery of the external surface 34 maintain contact with tissue in the left atrial appendage 5. Further, the curved external surface 34 may bias against tissue with the outward biasing force 17 along a circumferential surface area of the anchor portion, defined by a banded length 75 that may extend about a periphery or circumference of the anchor portion 16, as depicted in FIG. 7. The banded length 75 of the anchor portion 16 in biasing contact with the tissue 7 in the left atrial appendage 5 defines a banded portion or circumferential surface area of the external surface 34 of the anchor portion 16 in biasing contact with the tissue 7 such that opposing surfaces of the anchor portion 16 plug the left atrial appendage 5. Depending on the size of the anchor portion 16 or left atrial appendage 5, the banded length 75 may extend further, such as a full length 77 of the anchor portion 16, or a shorter length than that depicted. As such, the banded length 75 may be any length along the length 77 of the anchor portion 16, but preferably the banded length 75 is greater than half the length 77 of the anchor portion 16. Further, along with the external surface 34 of the anchor portion 16 being biased against the tissue 7 in the left atrial appendage 5, the external surface 34 of the anchor portion 16 may define the micro protrusions 35 (FIG. 1) or other structure that may assist in effectively engaging and grabbing tissue to hold the anchor portion 16 in the left atrial appendage 5. In this manner, the anchor portion 16 may be advanced from the catheter 82 and become lodged within the left atrial appendage 5 with the cover portion 14 still constricted in the distal end portion 84 of the catheter 82.

Figure 8:
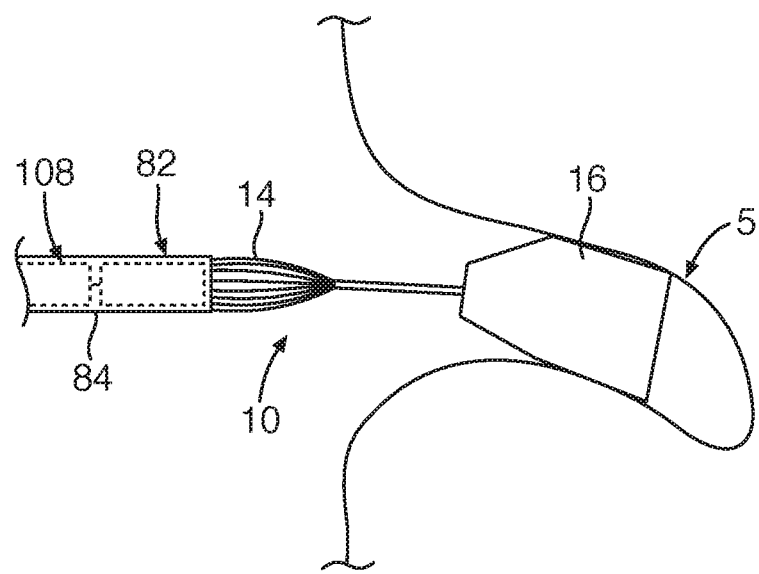
FIG. 8 is a side view of the distal portion of the delivery system, depicting a cover portion of the medical device being partially advanced from the distal portion of the delivery system adjacent the left atrial appendage.
Figure 9:
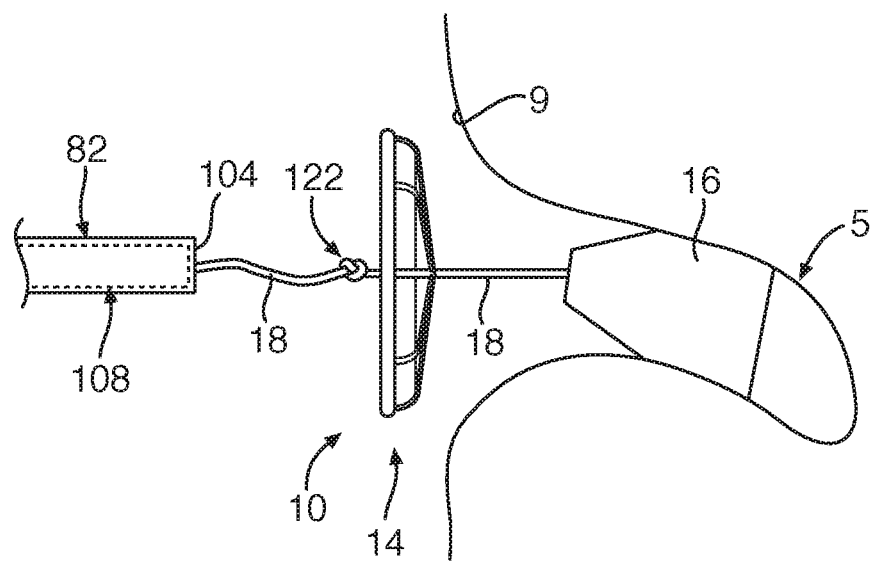
FIG. 9 is a side view of the distal portion of the delivery system and medical device, depicting the cover portion fully expanded with the delivery system coupled to the medical device with a flexible member, according to another embodiment of the present invention.
Figure 10:
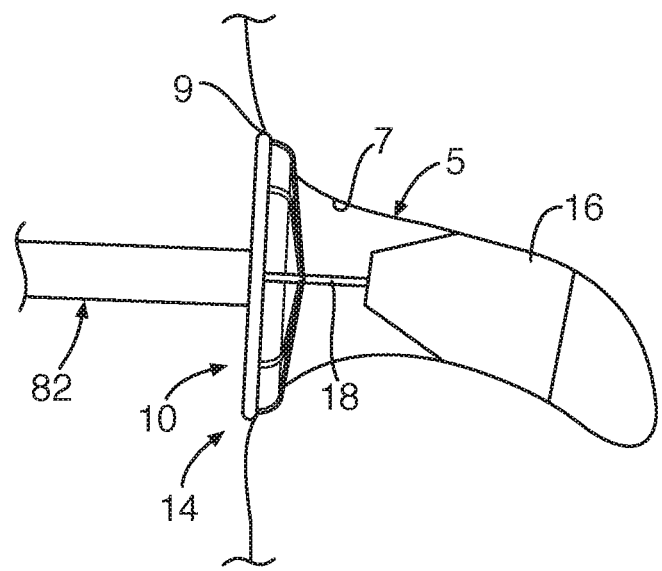
FIG. 10 is a side view of the distal portion of the delivery system and medical device, depicting the distal portion of the delivery system cinching the cover portion against the left atrial appendage with the flexible member, according to another embodiment of the present invention.

With reference to FIGS. 7-9, once the anchor portion 16 is positioned and anchored within the left atrial appendage 5, the physician may, for example, move or depress the switch 106 to then allow the pusher member 108 to move distally to a second hard stop for advancing the cover portion 14 from the distal end portion 84 of the catheter 82. As depicted in FIG. 8, the cover portion 14 is shown as being partially advanced from the distal end 104 of the catheter 82. Once the cover portion 14 is fully advanced from the catheter 82, as depicted in FIG. 9, the cover portion 14 of the medical device 10 may immediately self-expand to either be positioned against or spaced proximally of an ostium 9 of the left atrial appendage 5, as depicted. As previously set forth, the cover portion may self-expand via the expansion characteristics of the spokes 54 or outer lip 66 of the cover member, for example.

Figure 11:
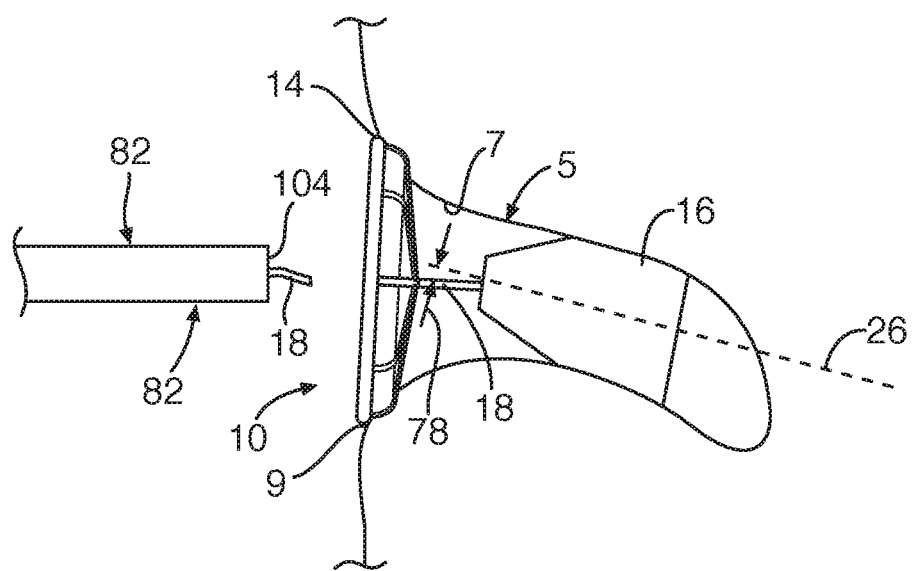
FIG. 11 is a side view of the distal portion of the delivery system and medical device, depicting the anchor portion anchoring the medical device in the left atrial appendage with the cover portion positioned over an ostium of the left atrial appendage, according to another embodiment of the present invention.

With respect to FIGS. 4, 9, 10 and 11, if the cover portion 14 is a spaced distance from the ostium 9, the physician may cinch the cover portion 14 against the tissue 7 defined by the ostium 9 of the left atrial appendage 5 via, for example, a slip knot 122 associated with the flexible member 18. The physician may actuate the switch 106 on the handle 86 and pull the pusher member 108 proximally, as shown with the bi-directional arrow 114. As the physician moves the pusher member 108 proximally, the cover portion 14 of the medical device 10 may be cinched against the ostium 9 of the left atrial appendage 5. Through this process, the distal end 104 of the catheter 82 may also push the cover portion 14 against the ostium 9 such that the cover portion 14 is positioned on an external side of the left atrial appendage 5, or against a proximal side of the ostium 9 of the left atrial appendage 5. Once the physician sufficiently cinches the cover portion 14 of the medical device 10 against the ostium 9 in a somewhat sealing manner, the switch 106 may be actuated so that the knob 112 of the pusher member 108 may be rotated, as shown by rotational arrow 116, to release the medical device 10 from the delivery system 80. For example, upon rotating the knob 112, a cutting or slicing mechanism (not shown) may be actuated to cut the flexible member 18 at a point proximal the cover portion 14 adjacent the hub 52 (FIG. 2) of the cover portion 14, as depicted in FIG. 11. The physician may then withdraw the catheter 82 from the heart and patient.

In this manner, the delivery system 80 may release the medical device 10 within the left atrial appendage 5 of a heart such that the anchor portion 16 may lodge the medical device 10 in the left atrial appendage 5 with the cover portion 14 sized and configured to seal and cover the ostium 9 of the left atrial appendage 5. Such cover portion 14 may be maintained against the ostium 9 of the left atrial appendage 5 due to the outward biasing force 17 of the anchor portion 14 against the tissue within the left atrial appendage 5 such that the anchor portion 14 maintains contact along opposing surfaces along a periphery of the external surface 34 of the anchor portion against the tissue so that the anchor portion 16 remains anchored in the left atrial appendage 5. Further, due to the flexible characteristics of the flexible member 18, the cover portion 14 may be oriented in various positions against the ostium 9 of the left atrial appendage 5 such that the flexible member 18 may extend tautly at an angle 78 relative to the axis 26 of the anchor portion 16. With this arrangement, the medical device 10 may close-off the opening of the left atrial appendage 5 in an atraumatic manner due to the anchor portion being anchored in the left atrial appendage 5 without hooks or tines, thereby, preventing perfusions that may otherwise occur.

Figure 12:
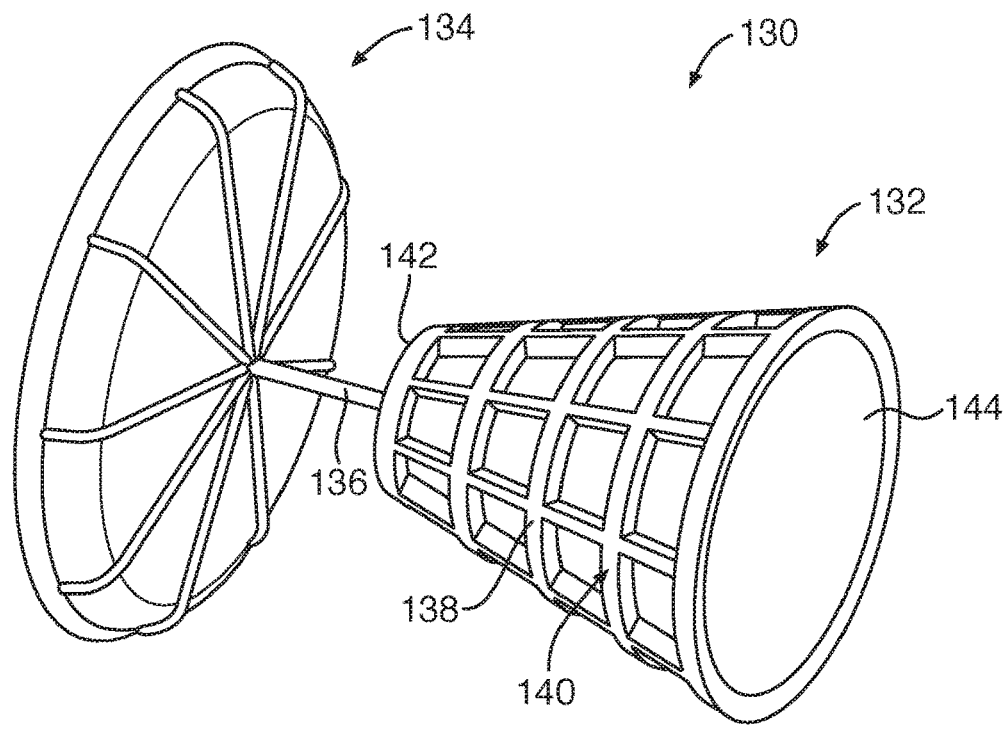
FIG. 12 is a perspective view of another embodiment of a medical device, depicting the anchor portion having a truncated cone structure with multiple recesses defined in an external surface of the anchor portion, according to the present invention.
Figure 13:
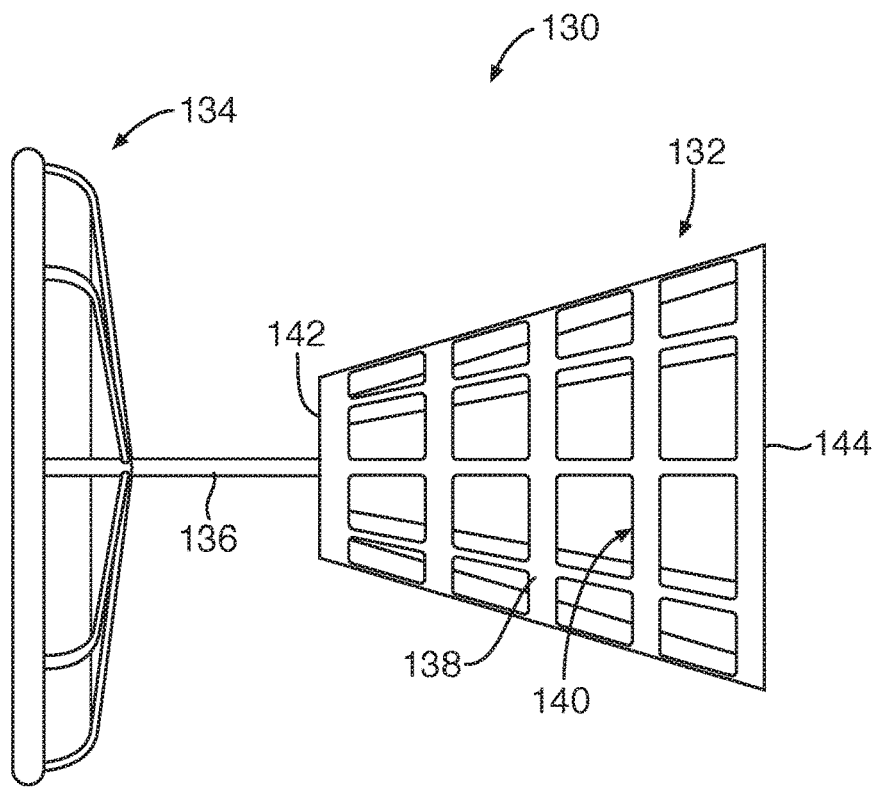
FIG. 13 is a side view of the medical device of FIG. 12, according to another embodiment of the present invention.

With respect to FIGS. 12 and 13, another embodiment of a medical device 130 is provided. This embodiment of the medical device 130 may include similar structural characteristics of the medical device described previously and may be employed in a similar manner with the delivery system 80 (FIG. 4), as previously set forth. The medical device 130 may include an anchor portion 132 and a cover portion 134 with a flexible member 136 coupled therebetween, similar to the previous embodiment. The anchor portion 132 may extend with a truncated cone structure, except in this embodiment, an external surface 138 of the anchor portion 132 may extend with a raised grid pattern 140. The raised grid pattern 140 may extend over a curved portion of the truncated cone structure between a proximal anchor end 142 and distal end 144 of the medical device 130. Such raised grid pattern 140 may be formed integrally with a foam material of the anchor portion 132. In one embodiment, the raised grid pattern 140 may be a continuation of the foam material. In another embodiment, the raised grid pattern 140 may be another polymeric material coupled to an underlining or core portion of the foam material of the anchor portion 132. As in the previous embodiment, the foam material of the anchor portion 132 may include micro protrusions along the external surface 138 of the anchor portion 132, including along the raised grid pattern 140. The raised grid pattern 140 of the anchor portion 132 may extend so that, upon being anchored in the left atrial appendage, the raised grid pattern 140 may facilitate grabbing portions of the external surface 138 in contact with tissue of the left atrial appendage. In this manner, and as in the previous embodiment, the anchor portion 132 with the raised grid pattern 140 may be conformable and resilient so that the anchor portion 132 may effectively be anchored within the left atrial appendage.

Figure 14:
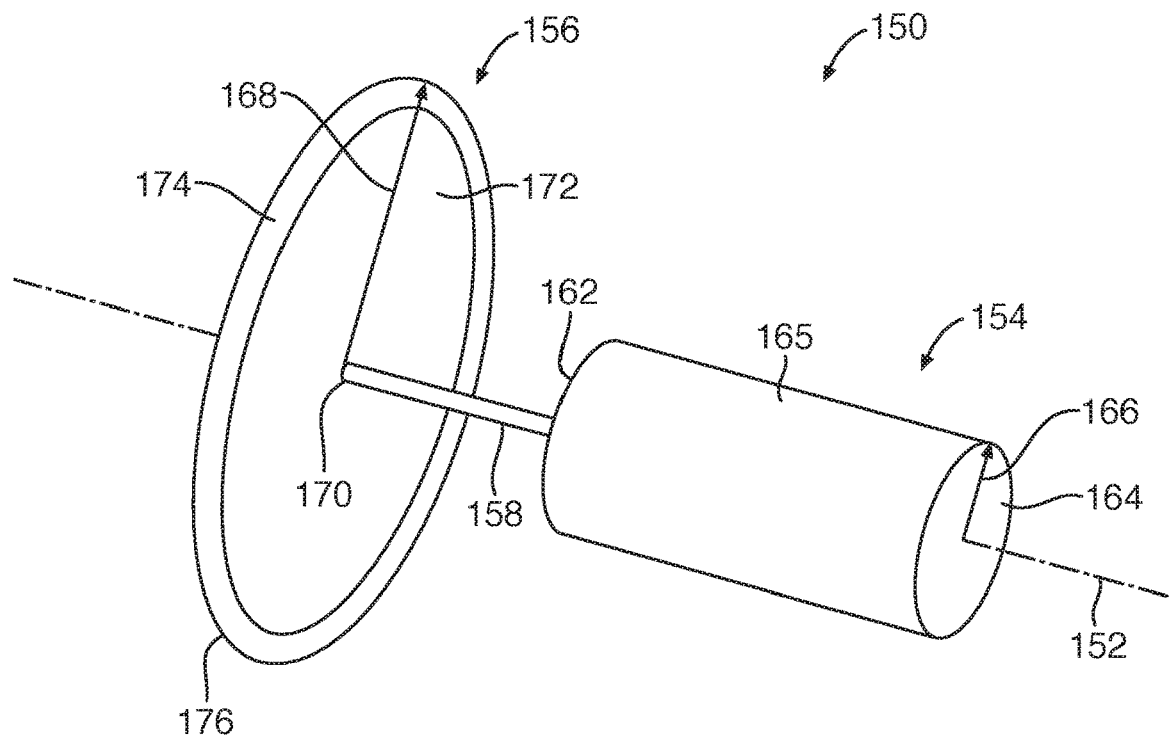
FIG. 14 is a perspective view of another embodiment of a medical device, depicting the anchor portion having a cylindrical structure and the cover portion extending with a disc structure, according to the present invention.
Figure 15:
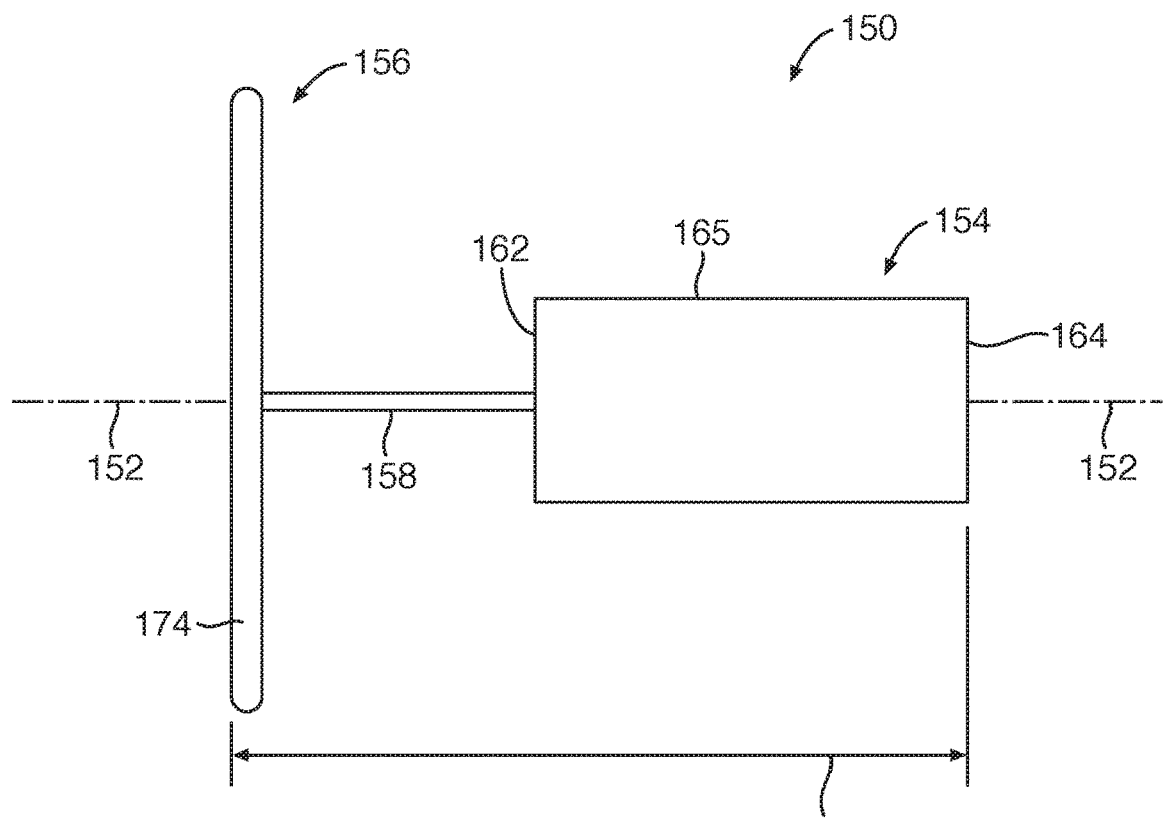
FIG. 15 is a side view of the medical device of FIG. 14, according to another embodiment of the present invention.

With reference to FIGS. 14 and 15, another embodiment of a medical device 150 is provided. Similar to the previous embodiments, the medical device 150 may define an axis 152 with an anchor portion 154 and a cover portion 156 with a flexible member 158 extending therebetween. The flexible member 158 may include similar structural characteristics as that described in previous embodiments.

In this embodiment, the anchor portion 154 may be a cylindrical structure sized and configured to be anchored within a left atrial appendage similar to the previous embodiments. Such cylindrical structure may be formed of a foam material. The cylindrical structure may include a length 160 extending between a proximal anchor end 162 and a distal end 164. The cylindrical structure may define an external surface 165 extending radially between the proximal anchor end 162 and the distal end 164 so as to define an anchor portion radius 166 along the length 160. As in the previous embodiments, the foam material of the anchor portion 154 may include micro protrusions along the external surface 165 of the anchor portion 132 to assist the anchor portion in grabbing tissue and lodging within the left atrial appendage with the outward biasing force of the foam material.

The cover portion 156 of this embodiment may be a disc structure defining a cover portion radius 168. The cover portion radius 168 may be equal to or larger than the anchor portion radius 166. The cover portion 156 may include a hub 170, a cover 172 and a lip 174. The hub 170 may be aligned with the flexible member 158 with the cover 172 extending radially from the hub 170. The lip 174 may extend with a ring shaped structure and may extend along an outer periphery 176 of the cover 172. The lip 174 and cover 172 may include similar materials as that described in the previous embodiments. The lip 174 may be sized and configured to self-expand from a constricted state to an expanded state, as depicted. In another embodiment, the cover portion 156 may include spokes extending from the hub 170 such that the spokes may extend radially relative from the hub 170 to the lip 174 of the cover portion 156. The spokes may operate similar to that described in previous embodiments, providing structural support and self-expanding characteristics.

Figure 16:
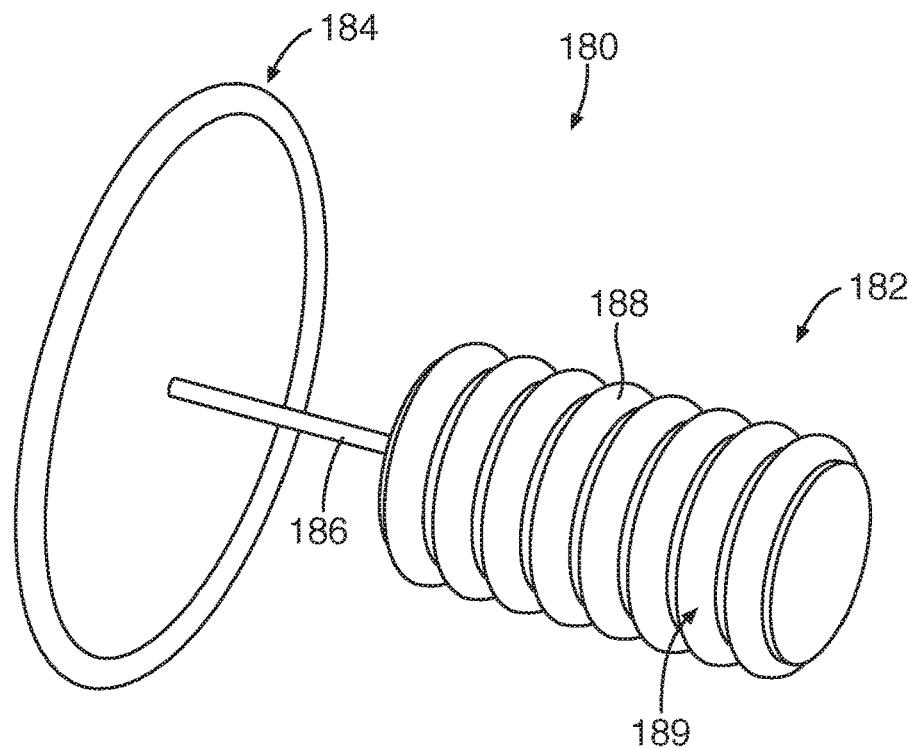
FIG. 16 is a perspective view of another embodiment of a medical device, depicting the anchor portion having a cylindrical structure with nub protrusions along an external surface of the anchor portion, according to the present invention.
Figure 17:
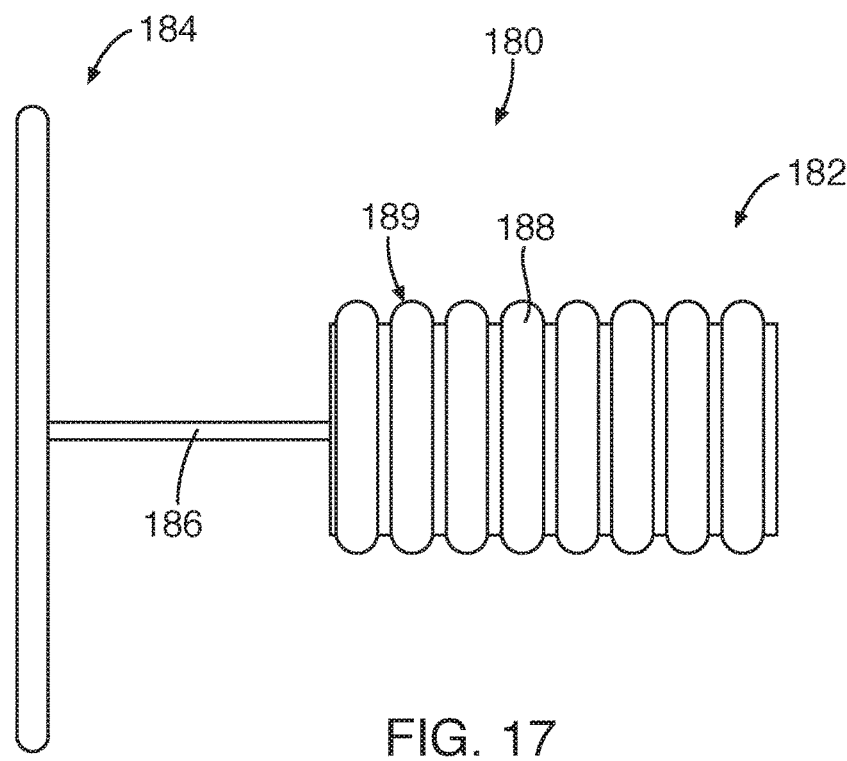
FIG. 17 is a side view of the medical device of FIG. 16, according to another embodiment of the present invention.

Now with reference to FIGS. 16 and 17, another embodiment of a medical device 180 sized and configured to occlude an opening, such as a left atrial appendage. The medical device 180 of this embodiment is similar to the previous embodiment, including an anchor portion 182 and a cover portion 184 with a flexible member 186 extending therebetween. In this embodiment, the anchor portion 182 may include a foam material defining a cylindrical like structure with an external surface 188 extending with multiple ring shaped structures 189 over the cylindrical structure. The foam material of the cylindrical structure and the ring shaped structures may include, as in previous embodiments, micro protrusions along the external surface 188 of the foam material to assist in grabbing tissue within, for example, the left atrial appendage. The ring shaped structures 189 may extend around the cylindrical structure in an evenly spaced manner. In another embodiment, the ring shaped structures 189 may extend around the cylindrical structure adjacently alongside each other. In another embodiment, the ring shaped structures 189 may extend with a gap or spacing between each of the ring shaped structures 189. Such ring shaped structures 189 also may assist in grabbing tissue with the outward biasing force of the foam material. The cover portion 184 and flexible member 186 may exhibit similar structural characteristics as described in previous embodiments.

Figure 18:
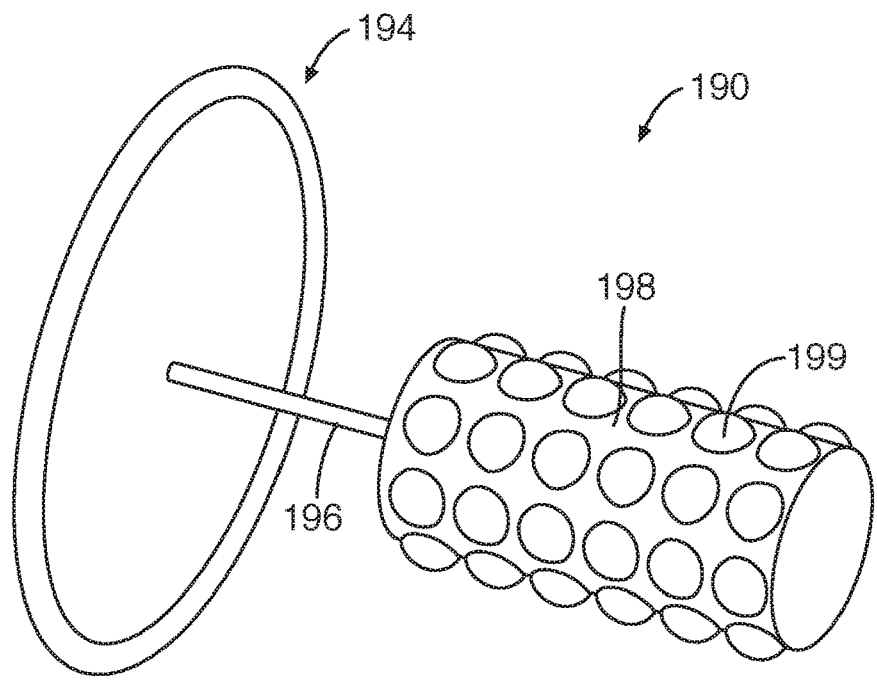
FIG. 18 is a perspective view of another embodiment of a medical device, depicting the anchor portion having a cylindrical structure with a ring configuration over an external surface of the anchor portion, according to the present invention.
Figure 19:
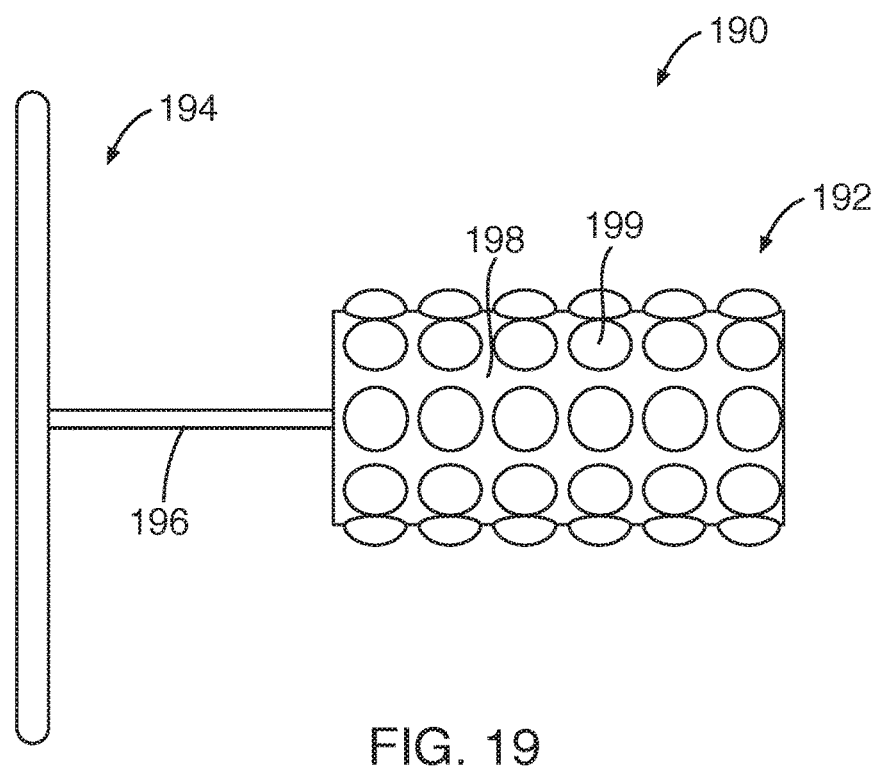
FIG. 19 is a side view of the medical device of FIG. 18, according to another embodiment of the present invention.

With reference to FIGS. 18 and 19, another embodiment of a medical device 190 is provided. In this embodiment, the medical device 190 may be substantially similar to the previous embodiment, including an anchor portion 192 and a cover portion 194 with a flexible member 196 therebetween. As in the previous embodiments, the anchor portion 192 may be formed of a foam material that may self-expand and provide the outward biasing force against tissue in the left atrial appendage. The anchor portion 192 may include a cylindrical structure, but instead of ring shaped structures, an external surface 198 of the cylindrical structure may include multiple protrusions 199 or nubs thereon. The protrusions 199 may be sized and configured to grab tissue with the outward biasing force of the anchor portion 192. Further, the protrusions and portions of the anchor portion surrounding the protrusions may include micro protrusions to assist in grabbing tissue, as described in previous embodiments. The protrusions 199 may be positioned in an aligned manner, such as rows, extending along a longitudinal length of the cylindrical structure. In another embodiment, the protrusions 199 may extend from the cylindrical structure in a random manner or staggered manner.

In another embodiment, the anchor portion of the various embodiments of the medical device set forth herein may be employed without the cover portion such that the medical device may act as a stand-alone plug to close-off the opening of the left atrial appendage. In this embodiment, the anchor portion may include similar structural characteristics as that described for the anchor portion of the various embodiments herein. Further, the proximal surface of the anchor portion or surface facing the left atrial chamber may be smooth and may be sized and designed to plug the ostium so that the proximal surface sits adjacent the ostium of the left atrial appendage.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes incorporating any portion of one embodiment with another embodiment, all modifications, equivalents, and alternatives falling within the spirit and scope of the invention as defined by the following appended claims.

What is claimed is:

1. A medical device for occluding a left atrial appendage of a heart, comprising:
   a cover portion having a hub and a cover, the cover extending radially from the hub, the cover portion sized and configured to be positioned along a proximal side of an ostium of the left atrial appendage; and
   a foam anchor portion coupled to the cover portion with a flexible member, the foam anchor portion extending between a proximal end and a distal end to define a length and an axis defined along the length of the foam anchor portion, the foam anchor portion defining a curved external surface radially extending relative to the axis such that the curved external surface extends between the proximal and distal ends of the foam anchor portion, the proximal end of the foam anchor portion extending to define a first radius and the distal end of the foam anchor portion extending to define a second radius, the second radius being greater than the first radius such that the curved external surface between the distal end and the proximal end extends with a truncated cone shape along an entirety of the length between the distal end and the proximal end, the foam anchor portion extending to define a raised grid pattern, the foam anchor portion configured to self-expand to provide an outward biasing force from the curved external surface such that a circumferential surface area of the curved external surface biases against tissue of the left atrial appendage.

2. The medical device of claim 1, wherein the curved external surface defines a total surface area, and wherein at least half of the total surface area of the curved external surface is sized and configured to grab and contact tissue within the left atrial appendage.

3. The medical device of claim 1, wherein the curved external surface of the foam anchor portion comprises micro protrusions sized and configured to grab and contact tissue within the left atrial appendage with the outward biasing force.

4. The medical device of claim 1, wherein the curved external surface of the foam anchor portion extends with the raised grid pattern and is sized and configured to grab tissue with the outward biasing force.

5. The medical device of claim 1, wherein the curved external surface of the foam anchor portion defines multiple protrusions sized and configured to grab and anchor to tissue with the outward biasing force.

6. The medical device of claim 1, wherein the curved external surface of the foam anchor portion defines multiple recesses therein, the multiple recesses defined by the raised grid pattern of the foam anchor portion.

7. The medical device of claim 1, wherein the curved external surface of the foam anchor portion defines multiple ring shaped structures.

8. The medical device of claim 1, wherein the foam anchor portion includes variable expandability between a proximal end portion and a distal end portion of the foam anchor portion, the distal end portion having greater foam expandability than the proximal end portion.

9. The medical device of claim 1, wherein the cover portion extends with a proximal facing surface having a concave structure, the proximal facing surface facing away from a distal end of the medical device.

10. The medical device of claim 1, wherein, upon the cover portion and the foam anchor portion being deployed, the flexible member is extendable at an angle relative to the axis of the foam anchor member.

11. A medical device system for occluding a left atrial appendage of a heart, comprising:
    a delivery device having a handle and a catheter extending between a proximal end and a distal end, the proximal end coupled to the handle, the catheter defining a lumen extending longitudinally through the catheter between the proximal and distal ends of the catheter; and
    a medical device operatively coupled to the handle, the medical device sized and configured to be moved between a constricted state and an expanded state such that, in the constricted state, the medical device is within a distal end portion of the catheter and, in the expanded state, the medical device is advanced from the catheter, the medical device comprising:
       a cover portion having a hub and a cover, the cover extending radially from the hub, the cover portion sized and configured to be positioned along a proximal side of an ostium of the left atrial appendage; and a foam anchor portion coupled to the cover portion with a flexible member, the foam anchor portion extending between a proximal end and a distal end to define a length and an axis defined along the length of the foam anchor portion, the foam anchor portion defining a curved external surface radially extending relative to the axis such that the curved external surface extends between the proximal and distal end of the foam anchor portion, the proximal end of the foam anchor portion extending to define a first radius and the distal end of the foam anchor portion extending to define a second radius, the second radius being greater than the first radius such that the curved external surface between the distal end and the proximal end extends with a truncated cone shape along an entirety of the length between the distal end and the proximal end, the foam anchor portion extending to define a raised grid pattern, the foam anchor portion configured to self-expand to provide an outward biasing force from the curved external surface such that a circumferential surface area of the curved external surface biases against tissue of the left atrial appendage.

12. The medical device system of claim 11, wherein the curved external surface defines a total surface area, and wherein at least half of the surface area of the curved external surface is sized and configured to grab and contact tissue within the left atrial appendage with the outward biasing force.

13. The medical device system of claim 11, wherein the curved external surface of the foam anchor portion comprises micro protrusions sized and configured to grab and contact tissue within the left atrial appendage with the outward biasing force.

14. The medical device system of claim 11, wherein, upon the cover portion and the foam anchor portion being deployed, the flexible member is extendable at an angle relative to the axis of the foam anchor member.

15. The medical device of claim 11, wherein the curved external surface of the foam anchor portion extends with the raised grid pattern and is sized and configured to grab tissue with the outward biasing force.

16. The medical device system of claim 11, wherein the curved external surface of the foam anchor portion defines multiple recesses therein, the multiple recesses defined by the raised grid pattern of the foam anchor portion.

17. The medical device system of claim 11, wherein the curved external surface of the foam anchor portion comprises multiple ring shaped structures.

18. The medical device system of claim 11, wherein the foam anchor portion includes variable expandability between a proximal end portion and a distal end portion of the foam anchor portion, the distal end portion having greater foam expandability than the proximal end portion.

19. The medical device system of claim 11, wherein the cover portion extends with a proximal facing surface having a concave structure, the proximal facing surface facing away from a distal end of the medical device.

* * * * *